(12) United States Patent
Tonner et al.

(10) Patent No.: US 11,585,213 B1
(45) Date of Patent: *Feb. 21, 2023

(54) METHOD AND APPARATUS FOR DRILL CUTTING ANALYSIS

(71) Applicant: Diversified Well Logging, LLC, Reserve, LA (US)

(72) Inventors: David Tonner, Houston, TX (US); Aaron Swanson, New Waverly, TX (US); Simon Hughes, Houston, TX (US)

(73) Assignee: DIVERSIFIED WELL LOGGING, LLC, Lafayette, LA (US)

( * ) Notice: Subject to any disclaimer, the term of this patent is extended or adjusted under 35 U.S.C. 154(b) by 183 days.

This patent is subject to a terminal disclaimer.

(21) Appl. No.: 17/155,183

(22) Filed: Jan. 22, 2021

Related U.S. Application Data

(63) Continuation of application No. 16/252,823, filed on Jan. 21, 2019, now Pat. No. 10,927,671.

(Continued)

(51) Int. Cl.
*E21B 49/00* (2006.01)
*G01N 33/24* (2006.01)
(Continued)

(52) U.S. Cl.
CPC .......... *E21B 49/005* (2013.01); *E21B 21/066* (2013.01); *E21B 49/02* (2013.01); *G01N 33/24* (2013.01)

(58) Field of Classification Search
CPC ...... E21B 49/005; E21B 49/081; E21B 49/08; E21B 43/26; E21B 49/02; E21B 49/10; E21B 7/04; E21B 47/10; E21B 49/00; E21B 43/00; E21B 44/00; E21B 47/00; E21B 49/087; E21B 21/01; E21B 21/06; E21B 21/067; E21B 21/08; E21B 47/022; E21B 47/04; E21B 49/0875; E21B 49/084; G01N 33/2823; G01N 24/081; G01N 33/241; G01N 1/24; G01N 1/286; G01N 1/4022; G01N 2001/4033; G01N 2015/1043; G01N 21/31; G01N 21/64; G01N 33/6848; G01N 3/08; G01N 3/12; G01N 3/40; G01N 24/10; G01N 33/0006; G01N 2021/1704; G01N 21/1702; G01N 21/274; G01N 21/552;
(Continued)

(56) References Cited

U.S. PATENT DOCUMENTS

| | | | |
|---|---|---|---|
| 8,619,256 B1 * | 12/2013 | Pelletier | C04B 40/0032 356/336 |
| 10,927,671 B1 * | 2/2021 | Tonner | E21B 21/066 |
| 2022/0003605 A1 * | 1/2022 | Harhira | G01J 3/0208 |

FOREIGN PATENT DOCUMENTS

| | | | | |
|---|---|---|---|---|
| CN | 114235871 A | * | 3/2022 | |
| DE | 102006059935 A1 | * | 6/2007 | .......... E21B 49/005 |
| WO | WO-2019246037 A1 | * | 12/2019 | .......... E21B 49/005 |

* cited by examiner

Primary Examiner — Andre J Allen
(74) Attorney, Agent, or Firm — Ted M. Anthony

(57) ABSTRACT

An automated or robotic mud-logger having a slurry sampler to collect a slurry sample online from a drilling fluid circuit contemporaneous with drilling of a borehole, the slurry sample including drilling fluid and rock cuttings. A liquid separator removes drilling fluid from the slurry sample and discharges a sample of the rock cuttings. A spectrometer performs elemental analysis of the sample of the rock cuttings substantially in real time with collection of the slurry sample.

20 Claims, 16 Drawing Sheets

Related U.S. Application Data

(60) Provisional application No. 62/622,740, filed on Jan. 26, 2018.

(51) Int. Cl.
*G01N 24/08* (2006.01)
*E21B 21/06* (2006.01)
*E21B 49/02* (2006.01)

(58) Field of Classification Search
CPC .... G01N 21/65; G01N 29/022; G01N 29/228; G01N 29/2418; G01N 29/46; G01N 30/02; G01N 11/00; G01N 11/10; G01N 11/14; G01N 13/02; G01N 15/088; G01N 1/10; G01N 2001/1031; G01N 2013/0283; G01N 2021/3595; G01N 2021/6417; G01N 2021/656; G01N 2030/025; G01N 2030/027; G01N 21/00; G01N 21/031; G01N 21/27; G01N 21/33; G01N 21/35; G01N 21/3504; G01N 21/3563; G01N 21/3577; G01N 21/59; G01N 21/77; G01N 21/85; G01N 21/8507; G01N 2201/06186; G01N 23/005; G01N 23/223; G01N 27/026; G01N 27/92; G01N 30/7206; G01N 33/0031; G01N 33/0047; G01N 33/0063; G01N 33/24; G01N 33/2835; G01N 33/2841; G01N 33/2882; G01N 33/383; G01N 9/36; G01N 2021/641; G01N 2021/06186
See application file for complete search history.

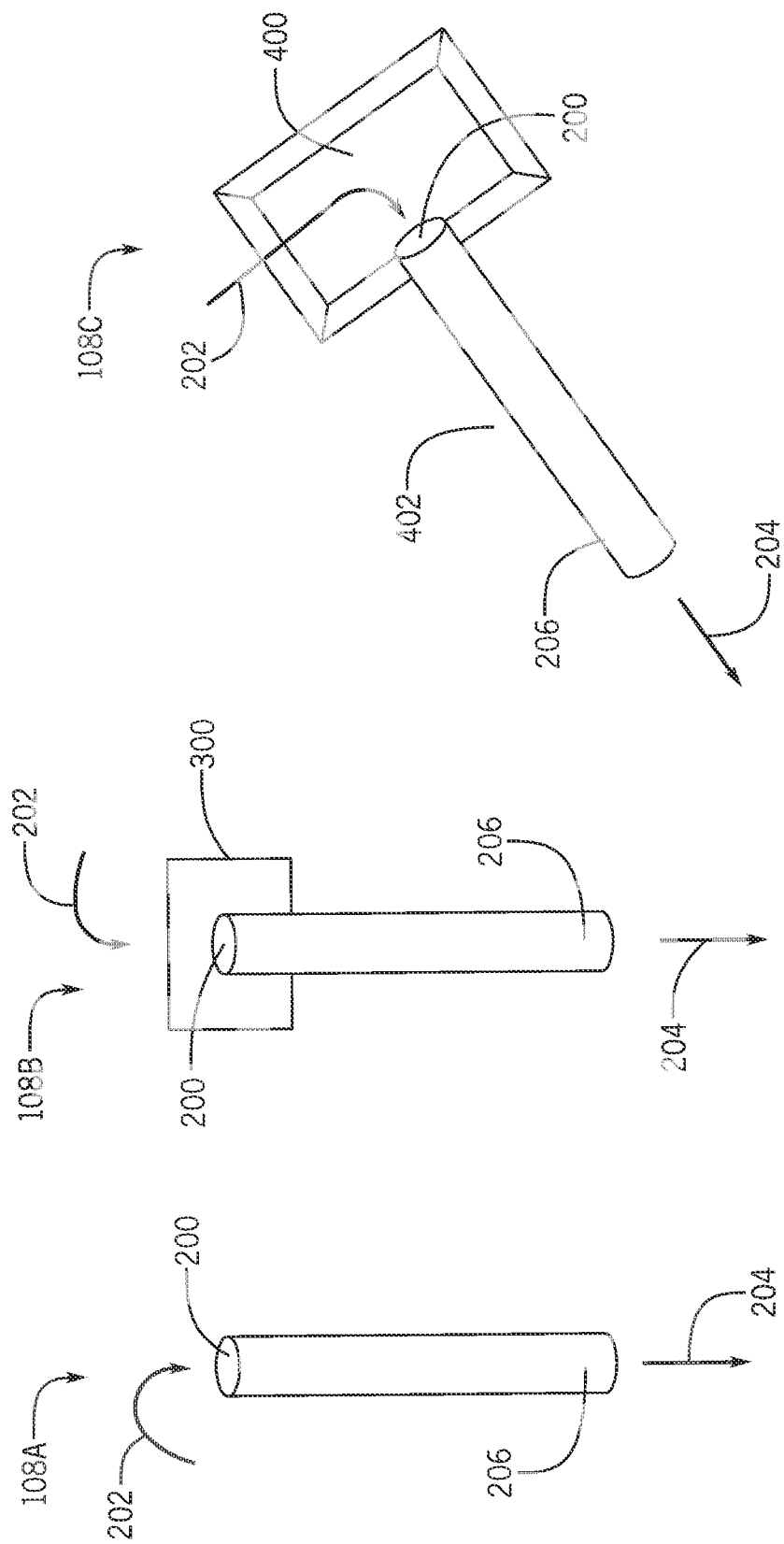

Lorem ipsum

METHOD AND APPARATUS FOR DRILL CUTTING ANALYSIS

CROSS REFERENCES TO RELATED APPLICATIONS

This application is a continuation of U.S. patent application Ser. No. 16/252,823, filed Jan. 21, 2019, currently pending, which application claims priority of U.S. PROVISIONAL PATENT APPLICATION Ser. No. 62/622,740, filed Jan. 26, 2018, all incorporated by reference herein.

STATEMENTS AS TO THE RIGHTS TO THE INVENTION MADE UNDER FEDERALLY SPONSORED RESEARCH AND DEVELOPMENT

NONE

BACKGROUND OF THE INVENTION

1. Field of the Invention

The present apparatus and techniques relate generally to the collection and analysis of drill cuttings from a borehole penetrating subterranean formations. More particularly, the present disclosure pertains to a robotic mud-logger that performs online elemental analysis of drill cuttings.

2. Description of Related Art:

This section is intended to introduce the reader to aspects of art that may be related to aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Mud logging or surface logging generally is the generation of a record or well log of a borehole by collecting and examining cuttings of rock brought to the surface by a circulating drilling medium (e.g., drilling fluid or drilling mud). A record or log may provide well owners and producers with information about the lithology and fluid content of a borehole and surrounding subterranean formations while drilling. In addition, for hydrocarbon exploration, hydrocarbon surface gas detectors may record the level of natural gas brought up in the mud. Frequently, a mobile laboratory may be situated near the drilling rig or on deck of an offshore drilling rig, or on a drill ship, and the like (typically by a mud logging company or entity). Mud logging is typically employed in petroleum exploration, but may also be employed when drilling water wells and in other mineral exploration where a drilling fluid or other circulating medium lifts rock cuttings out of a hole.

Conventional mud logging services are frequently focused on monitoring circulated drilling mud returns qualitatively for rock (cuttings) lithology, as well as oil and gas content. Such conventional mud logging may identify potentially productive hydrocarbon-bearing subterranean formations, identify marker or geological formations, and provide data to a driller to economically improve drilling operations. Moreover, conventional mud logging actions may include collecting, describing, and interpreting drill cuttings including in order document the type of minerals present and the rock lithology. Mud logging activities may also include estimating properties such as porosity and permeability of a drilled formation, maintaining and monitoring drilling-related sensing equipment, and estimating the pore pressure of a drilled formation.

Conventional mud logging actions may further include collecting, monitoring, and evaluating hydrocarbons released from drilled formations, assessing the productive capacity of hydrocarbon-bearing formations, and maintaining a record of drilling parameters. To this end, conventional mud logging services typically include observing mud returns for oil sheen, monitoring natural gas evolving from the mud at the surface, and examining the drill cuttings to determine rock type and for indication of oil in or on said cuttings. Gas chromatography was introduced in mud logging decades ago after electronics became sufficiently compact and rugged to be utilized in the field.

Generally, products delivered by a mud-logging vendor may include geological evaluation, petrophysical or reservoir formation evaluation, and drilling engineering support services associated with drilling and evaluation of wells. Such may support formation evaluation including building or refining the geological and reservoir models, and support drilling engineering and operations including the planning and execution of the well construction, and so forth.

In most cases, conventional mud logging involves the manual collection of samples, sieving, washing, cleaning and then analysis conducted by a geologist utilizing a microscope in order to generate a subjective sample description. Indeed, mud logging may involve a geologist collecting a sample, sieving and washing the rock, and making a manual description. This process, and the related analysis, may be subjective and prone to human error, and with low resolution on timing.

Lastly, logging while drilling may involve deployment of sensing tools in the drill string to make measurements downhole and transmit in real time to surface. Yet, these downhole techniques may be relatively expensive having lost-in-hole costs and also environmental considerations with respect to radioactive sources downhole.

SUMMARY OF THE INVENTION

An aspect of the present techniques relates to a robotic mud-logger having a slurry sampler to collect a slurry sample online from a drilling fluid circuit contemporaneous with drilling of a borehole, the slurry sample including drilling fluid and rock cuttings. The robotic mud-logger includes a liquid separator to remove drilling fluid from a slurry sample and discharge a sample of the rock cuttings. Further, the robotic mud-logger has a spectrometer to perform elemental analysis of the sample of the rock cuttings substantially in real time with collection of the slurry sample.

Another aspect of the present techniques relates to a drilling fluid system including a drilling fluid circuit and an automated mud-logger. The drilling fluid circuit circulates drilling fluid through a drilling rig at a borehole during drilling of the borehole. The automated mud-logger includes a slurry collector to acquire online a slurry sample of a drilling fluid slurry from the drilling fluid circuit, wherein the drilling fluid slurry includes drilling fluid and rock cuttings. The automated mud-logger includes a liquid separator to remove drilling fluid from the slurry sample and discharge a sample of the rock cuttings. The automated mud-logger has a conduit coupling the slurry sampler to the liquid separator. The automated mud-logger includes a platform to receive the sample of rock cuttings from the liquid separator; and an analyzer including a spectrometer to determine an elemental composition of the sample on the platform substantially in real time with acquiring of the slurry sample.

Yet another aspect of the present techniques relates to a method of operating a robotic mud-logger, including collecting, via a slurry sampler, a slurry sample online from a drilling fluid circuit contemporaneous with drilling of a borehole, the slurry sample having drilling fluid and rock cuttings. The method includes removing, via a liquid separator, drilling fluid from the slurry sample to give a sample of the rock cuttings. The method also includes determining, via an analyzer, an elemental composition of the sample of rock cuttings substantially in real time with the collecting of the slurry sample, wherein the analyzer comprises a spectrometer.

Yet another aspect of the present techniques relates to a robotic mud-logger having a slurry sampler to collect a slurry sample online from a drilling fluid circuit contemporaneous with drilling of a borehole, the slurry sample including drilling fluid and rock cuttings. The robotic mud-logger includes a liquid separator to remove drilling fluid from the slurry sample and discharge a sample of the rock cuttings. Lastly, the robotic mud-logger has a modular analyzer configured to receive measurement devices that determine properties of the sample of the rock cuttings.

BRIEF DESCRIPTION OF THE DRAWINGS

The foregoing summary, as well as any detailed description of the preferred embodiments, is better understood when read in conjunction with the drawings and figures contained herein. For the purpose of illustrating the invention, the drawings and figures show certain preferred embodiments. It is understood, however, that the invention is not limited to the specific methods and devices disclosed in such drawings or figures. Advantages of the invention may become apparent upon reading the following detailed description and upon reference to the drawings in which:

FIGS. 2 through 4 depict perspective views of slurry collectors of robotic mud-loggers in accordance with embodiments of the present techniques.

The same numbers are used throughout the disclosure and the figures to reference like components and features. Numbers in the 100 series refer to features originally found in FIG. 1; numbers in the 200 series refer to features originally found in FIG. 2; and so on.

DETAILED DESCRIPTION OF A PREFERRED EMBODIMENT

Figure 1:
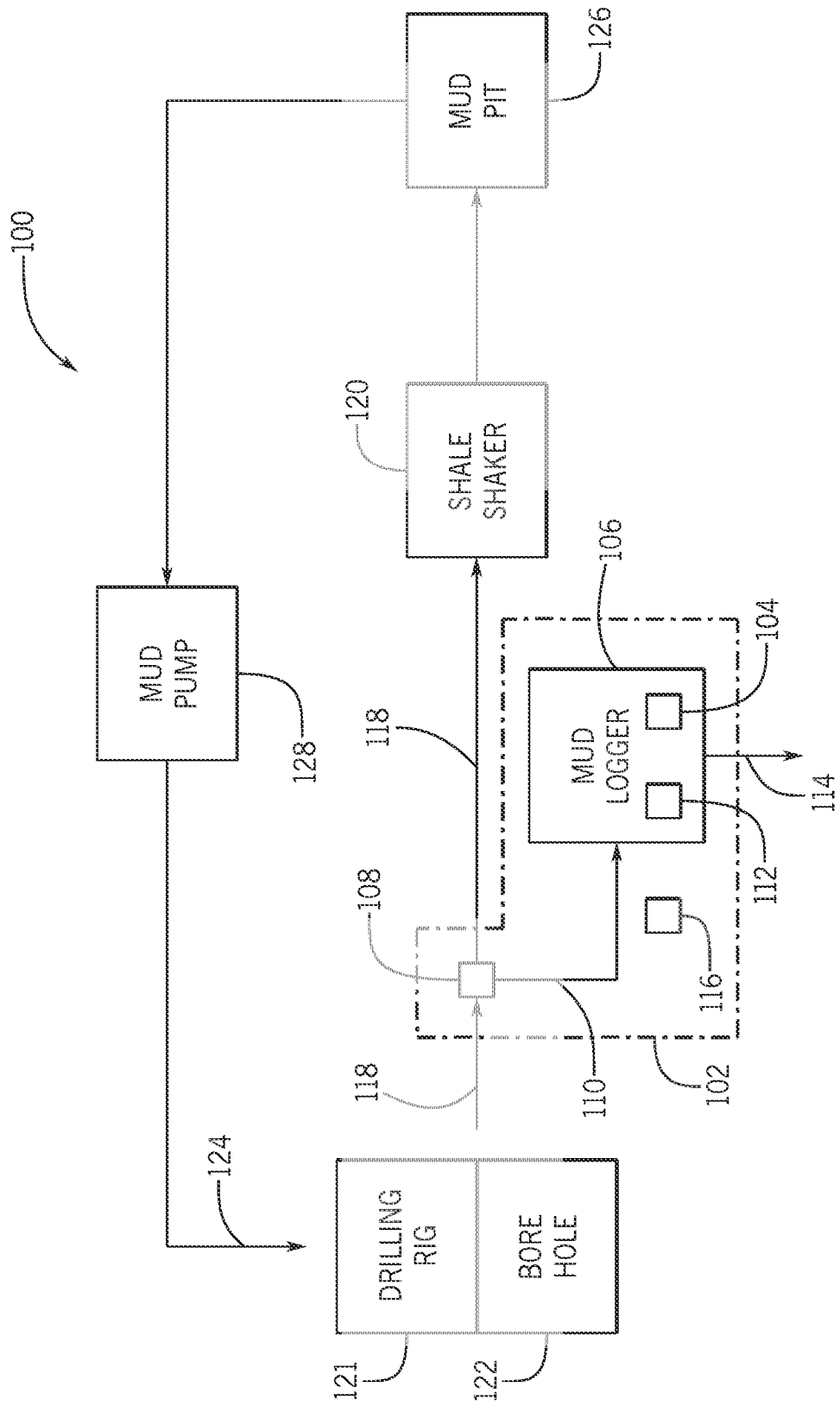
FIG. 1 depicts a block flow diagram of a drilling fluid system having a robotic mud-logger in accordance with embodiments of the present techniques.

One or more specific embodiments of the present invention will be described below. In an effort to provide a concise description of these embodiments, not all features of an actual implementation are described in the specification.

The present techniques relate generally to an automated mud-logger system to perform drill cuttings analysis associated with drilling of a well bore or borehole. Embodiments of the automated or robotic mud-logger perform collection and online elemental analysis of drill cuttings (rock cuttings) to determine an elemental composition of the drill cuttings. Indeed, embodiments of the present techniques relate generally to an automated device or system that may be characterized as a robotic mud-logger. As discussed below, the mud-logger device may have an extractor or slurry sampler to extract or collect a slurry sample of a slurry of drilling fluid and rock cuttings from a drilling fluid circuit. Example sample points in the drilling fluid system may be a drilling fluid return flow line or a shale shaker such as in the possum belly, and so on. In addition, a collection line or transfer conduit may convey or transport the slurry sample from the extractor to a main portion of the robotic mud-logger, such as to a liquid separator within a cabinet or housing of the robotic mud-logger. In some examples, one or more motive devices, such as pumps or ejectors, may facilitate transport or conveyance of the slurry sample and the subsequent removal of liquid (drilling fluid) from the slurry sample.

The automated or robotic device may include a liquid separator to remove the drilling fluid from the slurry sample and discharge a drill cuttings or rock cuttings sample. A variety of techniques may be implemented for the liquid separator. The robotic mud-logger may have an analyzer which may include or be a spectrometer. In a particular example, laser-induced breakdown spectroscopy (LIBS) is employed. In another particular example, the analyzer includes a Fourier-transform infrared (FTIR) spectrometer. Other types of cameras, spectrometers or analyzers may be employed. Additional aspects of the automated mud-logger may include return of the removed drilling fluid, storage of rock-cuttings samples, an imaging device(s), and so on.

An embodiment of a robotic mud-logger includes a slurry sampler to collect a slurry sample online from a drilling fluid circuit contemporaneous with drilling of a borehole, the slurry sample including drilling fluid and rock cuttings. In some examples, the slurry sampler may be installed inserted into a flow conduit or shale shaker of the drilling fluid circuit to collect the slurry sample. The robotic mud-logger may include a liquid separator to remove drilling fluid from the slurry sample and discharge a sample of the rock cuttings. Further, the robotic mud-logger has a spectrometer to perform elemental analysis of the sample of the rock cuttings substantially in real time with collection of the slurry sample. The elemental analysis may provide for an oxide weight percent for silicon dioxide ($SiO_2$), titanium dioxide ($TiO_2$), aluminum oxide ($Al_2O_3$), iron (III) oxide ($Fe_2O_3$), manganese oxide (MnO), magnesium oxide (MgO), calcium oxide (CaO), sodium oxide ($Na_2O$), potassium oxide ($K_2O$), or phosphorous pentoxide ($P_2O_5$), or any combinations thereof.

The spectrometer may be a Raman spectrometer, an FTIR spectrometer, a laser-induced breakdown spectrometer, or other type of spectrometer. Moreover, in certain embodiments, the spectrometer (which may be disposed in an analyzer housing) may have an electrical classification per National Fire Protection Association (NFPA) 70 of Class I, Division 1 or Class I, Division 2. In certain examples, the robotic mud-logger does not include a sample preparation system that alters form of the sample of rock cuttings. In other words, the spectrometer may determine the elemental composition of the rock cuttings in native or collected form as retrieved from the borehole.

The laser-induced breakdown spectrometer, if employed, may include a laser, mirror, and focusing lens. Laser-induced breakdown spectroscopy (LIBS) generally involves focusing a short laser pulse on a sample that then heats and atomizes, producing a localized plasma plume. Light from the plume is collected, dispersed by a spectrograph, and then typically focused on a charge-coupled device (CCD). The plume emits light whose wavelengths are characteristic of the atoms and ions present in the plasma, which in turn reflect the elemental composition of the sample. Therefore, LIBS may be a form of atomic emission spectroscopy.

The automated or robotic mud-logger may include a transfer or collection conduit coupling the slurry sampler to the liquid separator. In operation for some examples, a pressure differential from the drilling fluid circuit to the liquid separator drives flow of the slurry sample from the slurry sampler through the collection conduit to the liquid separator. The robotic mud-logger may have one or more motive devices (e.g., pumps, ejectors, etc.) to provide motive force for flow of the slurry sample from the slurry sampler through the collection conduit to the liquid separator.

The robotic mud-logger may have a surface or platform to support the sample of rock cuttings discharged from the liquid separator. The spectrometer may determine the elemental composition of the sample supported by the platform. The robotic mud-logger may include a sample storage system to receive the sample from the platform.

The robotic mud-logger may include a housing enclosing the spectrometer and the platform. In some examples, the housing has an electrical classification per NFPA 70 of Class I, Division 1 or Class I, Division 2. In addition, or in the alternative, the housing may satisfy similar standards from other countries and jurisdictions around the world such as in Europe or Asia. In one example in general, the robotic mud-logger or housing of the robotic mud-logger may have an electrical classification per National Fire Protection Association (NFPA) 70 National Electrical Code §500.7 Protection Techniques.

Furthermore, in certain examples, the robotic mud-logger may include one or more imaging devices to capture digital images of the sample and/or to perform image recognition on the sample to determine size, shape, color, or texture, or any combinations thereof, of the rock cuttings in the sample. The imaging device may be associated with a computing system of the robotic-mud logger. The computing system may have a processor and memory storing code executable by the processor for computer-implemented storage of digital images and performance of image recognition, and so on. The image recognition may generally identify and detect aspects of the rock-cuttings sample in the robotic mud-logger. In some examples, pattern matching, data analysis, visualization, comparative three-dimensional (3D) models, procedure development, and the like, may be employed in the image recognition. The detected features may be compared to known features data stored in computer memory. Moreover, machine learning or deep learning (e.g., neural networks) may be implemented for the image recognition is some examples. Indeed, the image recognition may, for instance, identify and extract features from images captured via the imaging device and input the extracted features to a machine learning model. Again, the image recognition may determine size, shape, color, or texture, and so forth, of the rock cuttings in the sample.

Moreover, the spectrometer or a second spectrometer of the robotic mud-logger may include a nuclear magnetic resonance (NMR) spectrometer to determine pore space size of the rock cuttings in the sample or identification of fluid in the sample, or other features. In general, as can be appreciated, NMR spectroscopy may determine physical or chemical properties. Indeed, in relying on the phenomenon of nuclear magnetic resonance, the NMR spectrometer or analyzer can provide information about structure and chemical environment. NMR spectra can be unique, well-resolved, analytically tractable and predictable. Thus, NMR analysis may confirm the identity of a substance. Different functional groups are generally distinguishable, and identical functional groups with differing neighboring substituents may give distinguishable signals. Moreover, as indicated, structure of porous media may be determined. Characteristics such as porosity, pore size distribution, permeability, fluid saturation, wettability, and so forth, may be evaluated. Again, the robotic mud-logger may include an NMR spectrometer to determine pore space size of the sampled rock cuttings or identification of fluid in the sample, or other characteristics.

Lastly, as indicated, the robotic mud-logger may include or be associated with a controller or computing system to direct or control operation of the robotic mud-logger. The one or more controllers or computing systems may be in the housing of the robotic mud-logger, local to the robotic mud-logger, or remote from the robotic mud-logger. The controlled operation may include sample handling and the spectrometer determining the elemental composition, as well as the control or direction of other equipment and actions. The robotic mud-logger may have a hardware processor to direct the analyzer and control an interval of collection of the slurry sample online from the drilling fluid circuit. The controller or computing system may include a hardware processor and memory storing code executable by the hardware processor to determine, via the spectrometer, the elemental composition of the sample of rock cuttings. The computing system or device may direct the spectrometer or an analyzer comprising the spectrometer.

Aspects of the present techniques may provide for automated collection of cutting samples produced during the drilling of a well. In an operating phase, an automated valve may collect a sample of fluid, including cutting samples, from a flow line from a drilling rig or at a shale shaker. During another operating phase, the automated valve may transfer or discharge the sample of fluid to a collection conduit. In some embodiments, a pump may move the sample of fluid through the collection conduit to a machine which seals the cuttings from the sample in a package and optionally labels the package. Some examples may realize advantages including more frequent cutting samples, even as drilling speeds increase. More frequent samples may facilitate identification of smaller oil and gas zones subsurface. The need for on-site human labor may generally be reduced. Optionally, some implementations allow for the storage of the cutting samples along with the collected liquid, which may maintain sample integrity over a longer period of time. Certain examples of the present device may facilitate collection and storage of well gas samples along with the cutting samples. In all, the techniques may facilitate increased automation and less people at the rig-site.

Data generated via certain embodiments of the present robotic mud-logger can be used to pick casing points, geo-stop wells, geo-steer wells, and coring points, identify hydrocarbon bearing zones, estimate geo-mechanical properties, and the like. The robotic mud-logger may be employed with high pressure—high temperature (HPHT) wells, high angle wells, coiled-tubing rig drilling, and so on. The system may involve integrating data in real time including connecting to real-time data feeds for electronic drilling recorders and gas detection systems. Indeed, various architecture may be leverage to provide for an integrated drilling and geological log in real time. In some examples, most or all data is collected and measured at surface and, thus, avoiding risks associated with down-hole devices. Again, the elemental data may be utilized to construct a chemo-stratigraphic framework and pick casing points, coring points, total depth (TD) wells, geo-steer wells, and with other actions.

Turning now to the drawings, FIG. 1 depicts a schematic view of a drilling fluid system 100 that may be characterized as a drilling fluid circuit associated with a drilling rig and the drilling of a well bore or borehole. The drilling fluid is generally liquid or slurry and may be labeled as drilling mud or other names. In some instances, compressed air or other mediums may be employed as a circulating fluid, rather than mud. In general, for geotechnical engineering, drilling fluid is utilized to drill boreholes into the earth including for oil and natural gas wells and for exploration drilling rigs, and for simpler boreholes such as water wells, and the like. The boreholes may be on land or off-shore. Drilling fluids may be water-based, non-aqueous, oil-based, synthetic, gaseous, and so forth. Drilling fluids may cool and clean the drill bit, carry drill rock cuttings to the surface, suspend the drill cuttings while drilling is paused, limit or reduce corrosion, provide hydrostatic pressure to inhibit formation fluids from entering into the well bore, and so on. Drilling fluids may help to control pressure in a well by offsetting pressure exerted by the hydrocarbons and the rock formations.

The example drilling fluid system 100 of FIG. 1 has a robotic mud-logger 102 device which may be an automated system for slurry sample collection and analysis of rock cuttings. The robotic mud-logger 102 has an analyzer 104 to perform elemental analysis of rock cuttings, as discussed below. In some embodiments, the analyzer 104 is disposed in a housing 106, e.g., an enclosure, cabinet, etc., of the mud logger 102. The analyzer 104 may be a modular analyzer configured to receive multiple measurement devices, as discussed below.

The mud logger 102 includes a slurry sampler or slurry collector 108 (e.g., an extractor with a collections box) to collect a sample of a slurry of circulating drilling fluid and rock cuttings. Examples of components of slurry collectors 108 are depicted in FIGS. 2 through 4.

In addition, the robotic mud-logger 102 has a transfer/collection conduit 110 (e.g., a collection line) to receive the slurry sample to an accumulation device or vessel, or to a collection box or liquid separator 112, and the like. In a particular example, the collection conduit 110 may operationally or fluidically couple the slurry collector 108 to the liquid separator 112 of the robotic mud-logger 102.

The liquid separator 112 if employed may be situated inside, partially inside, or outside of the housing 106. In the illustrated example, the liquid separator 112 is disposed within the housing 106. The liquid separator 112 may be a vessel, cyclone, centrifuge, filter, mesh, an assembly of multiple components, and so on. The liquid separator 112 may include enclosures, manifolds, baffling, piping, valves, chambers, and so forth, to facilitate separation of drilling fluid from the collected slurry sample. Indeed, in operation, the liquid separator 112 removes drilling fluid 114 from the slurry sample and discharges a sample of rock cuttings (drill cuttings) for analysis by the analyzer 104.

One or more motive devices 116 may promote flow of the slurry sample and the removal of the drilling fluid 114 from the slurry sample. The mud logger 102 may discharge the removed drilling fluid 114 as waste or as return to the drilling fluid circuit, and so on. Furthermore, the mud logger 102 may include mechanical conveying (e.g., conveying belt) or pneumatic conveyance systems, or other transport systems, to move the rock-cuttings sample within the housing 106. Motors, gears, blowers, dense-phase, dilute-phase, belts, and so forth, may be employed in the transport or conveying systems. Moreover, the mud logger 102 may store the sample of rock cuttings in certain embodiments.

As depicted, the slurry collector 108 may sample the slurry of drilling fluid and rock cuttings from a return conduit 118 of the drilling fluid system 100. Indeed, in this example, at least a portion of the slurry collector 108 is situated in the return conduit 118 to sample the slurry of the drilling fluid and the rock cuttings circulating from the borehole. In other examples, the slurry collector 108 may be disposed and sample at other portions of the drilling fluid circuit. For instance, in one example (not shown), the slurry collector 108 is situated in the shale shaker 120 or similar vessel of the system 100. In a particular example, the slurry collector 108 is situated in a possum belly of the shale shaker 120. Other slurry sample points in the drilling fluid system 100 may be accommodated, including before (upstream) or after (downstream) the shale shaker 120.

Furthermore, the interval of sample slurry collection may be controlled and adjusted, and may generally be a faster interval than typical manual collection of slurry samples from the drilling fluid system 100. Exemplary timing intervals for the on-line automated collection of the slurry sample may be in the range of 1 minute to 120 minutes, such as 3 minutes, 5 minutes, 10 minutes, 15 minutes, 20 minutes, 30 minutes, 45 minutes, and 60 minutes. Other timing for the sample interval, including values falling outside of this exemplary range, may be implemented. In one embodiment, the sample interval is substantially continuous (e.g., typically less than 5 or 10 seconds).

As for flow of the slurry sample from the drilling fluid circuit into and through the slurry collector 108, the robotic mud-logger 102 may rely on pressure in the drilling fluid circuit to provide a pressure differential for flow of the slurry sample through the slurry collector 108 to the liquid separator 112. As mentioned, the mud-logger 102 may include a motive component or device 116, such as a pump or eductor, to provide a motive force for flow of the slurry sample from the slurry collector 108 through the collection conduit 110 to the liquid separator 112.

In one example, the motive device 116 receives the slurry sample from the slurry collector 108, increases the pressure of the flowing slurry sample, and discharges the slurry sample to the liquid separator 112. Thus, in that example, the slurry sample may flow through the motive device 116. In other examples, the slurry sample does not flow through the motive device 116. Instead, in another example, the motive device 116 may inject clean fluid, such as diesel or water, into the collection conduit 110 or into the liquid separator 112 to pressurize and provide motive force for flow of the slurry sample through the collection conduit 110 and the liquid separator 112. In some examples, the motive device 116 may provide motive force for both separation of drilling fluid from rock cuttings in the liquid separator 112, and/or for discharge of the removed drilling fluid 114 from the mud-logger 102.

In certain examples, an additional motive component or device 116 downstream of the liquid separator 112 may further provide for hydraulic flow through the liquid separator 112 and discharge of the removed drilling fluid 112. The additional motive device 116 may be a pump, eductor, ejector, vacuum device vacuum pump, and the like.

In sum, the collected slurry sample may flow through the collection conduit 110 of the mud-logger 102 to the liquid separator 112, such as via the motive device 116 and/or via process pressure differential. In certain embodiments, the return flow conduit 118 may operate at higher operating pressure than the liquid separator 112. Again, a positive pressure differential between the return conduit 118 and the liquid separator 112 (or other receiving vessel or device) may drive fluid flow of the slurry sample through the transfer conduit 110 to within the housing 106 and may supplement the motive device 116 if a motive device 116 is employed.

In one embodiment, two motive devices 116 (e.g., pumps) are disposed in series. In that example, the first motive device 116 receives clean fluid (e.g., water, diesel, etc.) and pressurizes the robotic mud-logger 102 system. For instance, the first motive device 116 may pressurize the collection conduit 110, the liquid separator 112, and so on. In that example, the second motive device 116 if employed may evacuate the robotic mud-logger 102 system, such as evacuate the liquid separator 112, and discharge dirty fluid including the removed drilling fluid 114.

In a particular example, the collection conduit 110 may operate under pressure from the slurry collector 108 or collections box (or similar components) in the return conduit 118 or in the possum belly of the shale shaker 120. The slurry collector 108 may receive the collected slurry sample at a flow rate less than the volumetric flow rate pulled by the suction by the aforementioned second motive device 116 if employed. Control may be facilitated through, for example, a manifold within the robotic mud-logger 102 unit and the design of baffles within a collections box associated with the slurry collector 108, and so on.

In general, the drilling fluid system 100 may supply drilling fluid to a drilling rig 121 forming a well bore or borehole 122; in many cases, drilling fluid system 100 may be viewed as a component part or subsystem of a drilling rig 121. The example of the drilling fluid system 100 depicted in FIG. 1 provides the drilling fluid via a supply conduit 124. As discussed, the drilling fluid system 100 has the return flow conduit 118 to receive drilling fluid and rock cuttings from the drilling rig 121 and borehole 122. This slurry of return drilling fluid and recovered rock cuttings may be conveyed via the return conduit 118 to the shale shaker 120 in the illustrated example. The shale shaker 120 may remove rock cuttings from the slurry and discharge the circulating drilling fluid to one or more mud pits 126 and/or similar vessels. Further, additional components of the drilling fluid system 100 may treat or otherwise process the drilling fluid. In addition, the drilling fluid circuit 100 may include one or more mud pumps 128 to provide the drilling fluid via the supply conduit 124 to the drilling rig 121. Lastly, as should be understood for clarity, not all components of a drilling fluid system 100 are depicted in FIG. 1.

Components of a shale shaker 120 or similar shaker may include a hopper, feeder, sieve, screen, screen mesh, screen basket, basket angling mechanism, vibrator, screen frame, binding agent, 3D screen technology, and so on. A shaker or shale shaker, such as the depicted shale shaker 120, in a drilling fluid system may provide for solids control of rock cuttings removed from the borehole 122, including separating rock cuttings from the drilling fluid. As indicated, drilling fluids, which may be a mixture of various chemicals in a water or oil based solution, may serve to lubricate and cool the drill bit as well as convey the drilled cuttings away from the borehole 122. Drilling fluid losses may be reduced by recovering the drilling fluid from the drilled rock cuttings before the cuttings are disposed. This may be performed by employing a multitude of specialized machines and tanks. In this context, shale shakers may be a primary or important solids separation tool.

In operation, the drilling fluid may return from the well borehole 122 to the surface of the well and flow to the shale shaker(s) 120 that processes the drilling fluid. Once processed by the shale shakers, the drilling fluid may be deposited into mud tanks 126 (also sometimes referred to as a "mud pit") where other solid control equipment may begin to remove finer solids from the drilling fluid. In some examples, the solids removed by shale shaker 120 may be discharged into a separate holding tank where the solids await further treatment or disposal. Human mud-loggers may go on-site to the shaker 120 and manually check the shaker 120 for rock samples, separate the manually-collected sample of rock cuttings from the drilling fluid, and take the rock cuttings to a local lab. At the lab, the samples may be, for example, dried and labeled according to depth, visually analyzed, etc.

A possum belly may be a metal container at a head of the shale shaker 120 that receives the flow of drilling fluid and is coupled (e.g., directly connected) to an end of the return flow line 118. A possum belly may also be referred to as a distribution box or flowline trap. A purpose of the possum belly may be to slow the flow of the drilling fluid. The possum belly may be considered to have derived its name from the similarity of its appearance to the underbelly of the female possum.

FIGS. 2 through 4 are alternative embodiment examples of the slurry collector 108 (108A, 1088, 108C, respectively) which may generally be or include a sample conduit having an opening 200 at one end to receive and collect the slurry sample, as indicated by arrow 202. The sample conduit may be piping, tubing, etc. As discussed, the collected slurry sample may be a sample of the circulating slurry of drilling fluid and rock cuttings. As also discussed above with respect to FIG. 1, the slurry collector 108 may receive this slurry sample from the drilling fluid circuit, such as from the return conduit 118 or the shale shaker 120, and the like. The sample collector 108 may discharge the slurry sample, as noted by arrow 204, to the transfer/collection conduit 110 shown in FIG. 1. The distal end 206 of the collector 108 conduit may have or be associated with a coupling or connector to attach or otherwise couple the collector 108 to the transfer conduit 110.

An exemplary nominal diameter or inside diameter of the collector 108 sample conduit may be in a range of about 0.5 inch to about 4.0 inches. Example nominal values include about 0.75 inch, 1.0 inch, or 1.5 inch, and the like. The collector 108 conduit may have other nominal diameters including values that fall outside this exemplary range. Moreover, the collector 108 sample conduit may have a geometry other than cylindrical, such as rectangular, irregular, or other geometries.

The example sample collector 108B of FIG. 3 includes a tip or shield 300 disposed on the collector 108B sample conduit. The shield 300 may be perforated or slotted with openings (e.g., holes, apertures, slots, perforations, gaps, etc.) that allow the slurry sample 202 to flow into the opening 200 of the conduit. The shield 300 openings may be sized to block or exclude relatively large solid particles in the slurry from entering the conduit opening 200.

The example sample collector 108C of FIG. 4 has a protrusion 400 disposed on or coupled with the collector 108C sample conduit 402 to facilitate collection of the slurry sample. The protrusion 400 may be an extension, extender, projection, ledge, tip, lip, pan, etc. that may promote collection and entry of the slurry sample into the opening 200 of the collector 108C sample conduit 402. In some examples, the protrusion 400 has a surface(s) to advance collection and receipt of the slurry sample. In the illustrated example of FIG. 4, the protrusion 400 is a sample board having a pan shape to collect and direct the slurry sample toward the opening 200 of the conduit 402. In one example, the protrusion 400 may collect the slurry sample from within the shale shaker 120 (e.g., within the possum belly). The shaker board design and mounting system may be adjusted as desired. Moreover, in response to low rates of penetration (ROP), the sample board may be placed on the end of the shale shaker instead of in the possum belly of the shale shaker to facilitate collection an adequate amount of rock cuttings.

Further, the protrusion 400 (e.g., pan or sample board) may include additional openings, and/or couplings to other conduits. Such may be for receipt or discharge of processing fluid, gas, air, slurry, etc. for handling of the slurry sample and processing (e.g., cleaning, clearing, etc.) of the surrounding area or volume (e.g., in the shale shaker 120) in the drilling fluid circuit. Lastly, it should be emphasized that the depictions in FIGS. 2 through 4 are given only as illustrative examples and should not be viewed or construed as limiting. Other configurations and techniques for an extractor or sample collector 108 are applicable.

Figure 5:
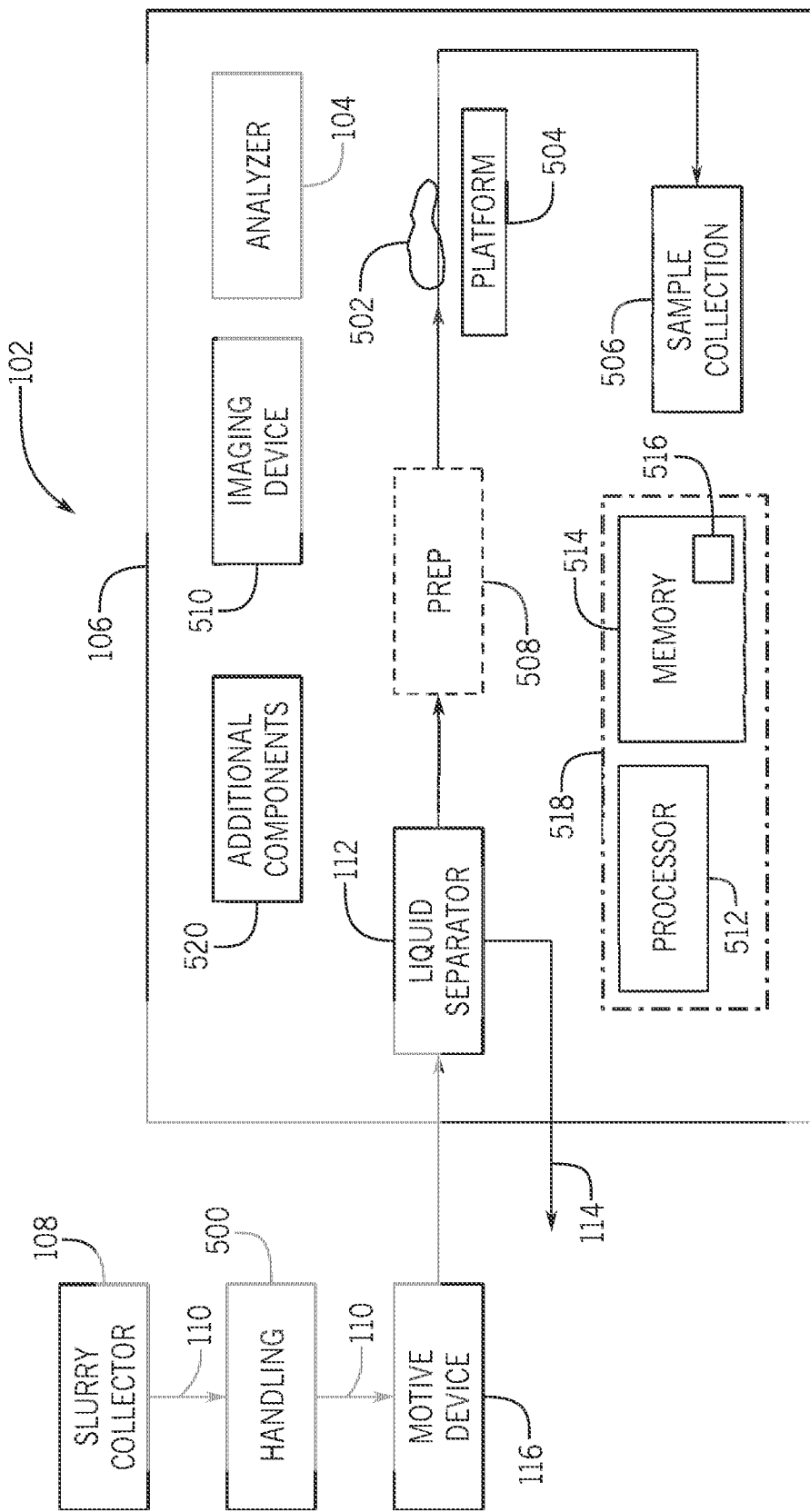
FIG. 5 depicts a block diagram of the robotic mud-logger of FIG. 1 in accordance with embodiments of the present techniques.

FIG. 5 depicts a schematic view of an example of the robotic mud-logger 102 which may include a handling system 500 for collecting and handling a slurry sample. The handling system 500 may include piping, valves, manifolds, baffles, actuators, chambers, and the like. The handling system 500 may be associated with the slurry collector 108, or disposed along the transfer conduit 110, and/or in the housing 106, and so forth. Indeed, the handling system 500 may include components or portions along the transfer conduit 110 and also inside, for example, the cabinet or housing 106 of the robotic mud-logger 102, to facilitate handling of the slurry sample and implementation of a sampling duty cycle. In one example, the handling system 500 includes a multi-port manifold with actuators inside the housing 106 that directs fluid flow. Moreover, the handling system 500 may rely on or utilize other features such as the motive device 116 and the transfer conduit 110, and so on.

In examples, the slurry collector 108 or extractor sits at the flow line 118 or at the possum belly of the shaker 120, and the like. The extractor may have a conduit (e.g., a hose) that extends into the possum belly and directs purge flow and suction to collect the slurry sample including the rock cuttings. A casing or box may be associated with or encompass the extractor. Additional conduits may couple with the box, such as for purge, suction, etc. The box itself may include a series of chambers and baffles that direct flow.

In operation, the handling system 500 or other components may provide for a sampling duty cycle including, for example, phases of purge and collect. A purge phase may be implemented to clear away rock cuttings at the sample collector 108 before or after the collect phase of the slurry sample. In some examples, the purge phase or purge cycle may act as a jet or spurt through the transfer conduit 110 and sample collector 108 into the drilling fluid circuit where the sample collector 108 is situated, such as into the flow line 118 or into the possum belly of the shale shaker 120. The purge or jet may clear residual slurry sample from the volume in the drilling fluid circuit around the sample collector 108.

In one embodiment, the duty cycle may include collect and then purge. In other words, the sample collector 108 may gather a slurry sample, and then purge an area or volume in the drilling fluid circuit at the collector 108 to clear remnants of gathered samples, so that future samples collected will be representative of the timing. In general, a sampling duty cycle associated with the sample collector 108 may refer to action of clearing conduits and collecting the sample.

In some examples, the duty cycle may include at least four phases. In a particular example, the four or more phases may include purge, sample, dry, clean-out, etc. that can be manually implemented or more-typically controlled by a computing system associated with the robotic mud-logger 102. The purge may force fluid (e.g., liquid or relatively clean drilling fluid) from a supply pump (e.g., motive device 116) at the mud-logger 102 back through the transfer conduit 110 to substantially clear any previous sample collection remaining in the transfer conduit 110. The sample phase may be characterized as somewhat as a purge in reverse in some instances. The sample phase may draw cuttings and drilling fluid from the possum belly (of the shale shaker 120) or from the flow line 118 through the motive component 116. In certain examples, the sample phase of the sampling duty cycle forces the slurry sample into a collection box or liquid separator 112 in the housing 106 of the mud logger 102. A dry phase if implemented in the sampling duty cycle may generate a suction at the internal collection box or liquid separator 112 to pull the drilling fluid 114 to a second motive component or pump that discharges the removed drilling fluid 114. A clean-out phase if implemented may be a relatively short phase generally independent of the dry phase to substantially prevent or reduce backflow from siphon action, for example.

As discussed, the liquid separator 112 may remove drilling fluid 114 from the slurry sample and discharge a rock-cuttings sample 502 for analysis by the analyzer 104. The rock-cuttings sample 502 may have residual drilling fluid. In the illustrated embodiment, the robotic mud-logger 102 includes a surface or platform 504 to receive the rock-cuttings sample 502. The robotic mud-logger 102, via its analyzer 104, may perform elemental analysis or other analyses on the sample 502 of rock cuttings on the platform 504. In some examples in which mechanical conveying is employed, the sample 502 may reside on a conveying component (e.g., a conveying belt and/or mesh) that is situated on the platform 504. Motors, gears, and so forth, may be employed.

In other examples, a platform 504 is not employed. Instead, the analyzer 104 may receive the rock-cuttings sample 502 to a surface or volume in the analyzer 104. Moreover, the mud logger 102 may include a sample collection system 506 to store the rock-cuttings sample 502 for later retrieval for analysis, for example, outside of the mud logger 102, such as in a laboratory or a mobile analysis unit situated local or remote.

In examples, the analyzer 104 may be or include a spectrometer, such as a Raman spectrometer, a FTIR spectrometer, a laser-induced breakdown spectrometer, or other type of spectrometer. The analyzer 104 (e.g., spectrometer) may perform elemental analysis of the sample 502 of rock cuttings. The mud logger 102 may include a sample preparation system 508 to condition or prepare (e.g., wash, grind, mold, etc.) the sample 502 prior to analysis. In one example, the sample preparation system 508 (if employed) may have spray jets of water for water-based muds and other chemicals, such as detergents or diesel, for oil-based mud systems.

However, some embodiments do not include the sample preparation system 508. In other words, for those embodiments, the robotic mud-logger device 102 which removes drilling fluid from the slurry sample to give a rock-cuttings sample 502 does not alter or substantially alter the form of the rock cuttings. Indeed, the analyzer 104 or spectrometer may determine the elemental composition of the rock cuttings in sample 502 in collected form as retrieved from a borehole 122 (depicted in FIG. 1). For instance, the sample 502 is not grinded or molded. Such may be the case, for example, with the analyzer 104 as a laser-induced breakdown spectrometer.

Laser-induced breakdown spectroscopy is generally a type of atomic emission spectroscopy employing an energetic laser pulse as the excitation source. The laser is focused to form a plasma atomizing and exciting samples to perform optical emission spectrometry. The formation of the plasma begins when the focused laser achieves a threshold for optical breakdown. Because most or all elements of the sample emit light of characteristic frequencies when excited to sufficiently high temperatures, the spectrometer can generally detect most or all elements, limited by power of the laser as well as sensitivity and wavelength range of the spectrograph and detector. If the constituents of a material to be analyzed are known, laser-induced breakdown spectroscopy may evaluate the relative abundance of each constituent element, or to monitor the presence of impurities. In practice, detection limits may be a function of the plasma excitation temperature, the light collection window, the line strength of the viewed transition, and so forth.

The robotic mud-logger 102 may also include one or more imaging devices 510 to capture images or photos of the rock-cuttings sample 502. The one or more imaging devices 510 may include an imaging device 510 to perform image recognition on the sample to determine size, shape, color, or texture, or any combination thereof, of the rock cuttings in the sample. Furthermore, an imaging device 510 may provide for ultraviolet (UV) imaging of the rock-cuttings sample 502. An imaging device 510 may include a microscope. Moreover, the analyzer 104 may include an NMR spectrometer to determine pore space size of the rock cuttings in the sample or identification of fluid in the sample, or other features.

The robotic mud-logger 102 may include a hardware processor 512 and memory 514. The processor 512 may be a microprocessor, central processing unit (CPU), or other types of circuitry. The memory 514 may include volatile memory and non-volatile memory, and other types of memory. The memory 514 may store code 516 (e.g., instructions, logic, etc.) executed by the processor 512 in the control of the robotic mud-logger 102. In some examples, the processor 512 and memory 514 may be collectively referred to as a controller or computing system 518. The robotic mud-logger 102 or computing system 518 may include an integrated circuit, a printed circuit board (PCB), a printed circuit assembly (PCA) or printed circuit board assembly (PCBA), an application-specific integrated circuit (ASIC), a programmable logic controller (PLC), a component of a distributed control system (DCS), a field-programmable gate array (FPGA), or other types of circuitry. Firmware may be employed. In some cases, firmware if employed may be code embedded on the controller such as programmed into, for example, read-only memory (ROM) or flash memory. Firmware may be instructions or logic for the controller hardware and may facilitate control, monitoring, data manipulation, and so on, by the controller.

The computing system 518 may be communicatively coupled with components of the robotic mud-logger 102 and with devices remote from the robotic mud-logger 102. Moreover, remote computing systems may also supplement control of the robotic mud-logger 102.

Computerized data acquisition and the routine transfer of acquired data to a datacenter may facilitate additional interpretive techniques and the integration of data from different sources into the geological and reservoir model, including in near real time in some examples. This, coupled with measurement-while-drilling (MWD) and logging-while-drilling (LWD) tools, may provide for the mud-logging unit as a hub for rig-site data gathering and transmission. Such may facilitate the geologist and petroleum engineer to interpret and integrate geological, drilling, and geochemical data.

The robotic mud-logger 102 may include additional components 520, such as lighting, an on-line x-ray fluorescence (XRF) device, an on-line x-ray diffraction (XRD) device, a pyrolysis device, and the like. In general, the robotic mud-logger 102 may emulate observation of fluorescence as observed by a human mud-logger. Further, additional components 520 may include systems (e.g., having motors, gears, belts, etc.) to convey the rock-cuttings sample 502, as well as include items such as rollers, plastic, sample bags, labels, etc. to supplement the sample collection system 506 in the saving and storing of the rock-cuttings samples 502.

As mentioned, various sample points in the drilling fluid system 100 for the slurry of drilling fluid and rock cuttings may be implemented. Certain embodiments of the robotic mud-logger 102 provide for sampling from a low-pressure side of a Managed Pressure Drilling (MPD) system. In some examples, the high-pressure side of the MPD system may greater than, for instance, 200 pounds per square inch gauge (psig) and the low-pressure side of the MPD system less than 200 psig. The robotic mud-logger via its slurry collector 108 and/or other components may sample rock cuttings, drilling fluid, gas, etc. from the low-pressure side of an MPD system. MPD may provide a closed-loop circulation system in which pore pressure, formation fracture pressure, and bottomhole pressure are balanced and managed at surface. Indeed, MPD may provide an active approach to well control. Unlike passive control methods, MPD operations employ the closed-loop system that facilitate determining of the downhole pressure limits and managing the annular pressure profile accordingly.

As discussed above with respect to FIG. 1, flow of the slurry sample from various sample points in the drilling fluid system 100 may rely on pressure in the drilling fluid circuit. Indeed, the pressure in the drilling fluid circuit may provide a pressure differential for flow of the slurry sample into and through the slurry collector 108 to the liquid separator 112. As mentioned, the mud logger 102 may include a motive component or device 116, such a pump, eductor, or ejector, to provide a motive force for flow of the slurry sample from the slurry collector 108 through the collection conduit 110 to the liquid separator 112. In one example, the slurry sample flows through the motive device 116. In other examples, the slurry sample does not flow through the motive device 116. Instead, the motive device 116 may inject, for instance, drilling fluid into the collection conduit 110 or into the liquid separator 112 to pressurize and provide motive force for flow of the slurry sample through the collection conduit 110 and the liquid separator 112. The motive device 116 may provide motive force for separation of drilling fluid from the rock cuttings in the liquid separator 112, and for discharge of the removed drilling fluid 114 from the mud logger 102. More than one motive component or device 116 may be employed. Motive devices 116 may push and/or pull removed drilling fluid from the liquid separator 112.

Lastly, certain embodiments of the automated or robotic mud-logger 102 may be a modular device, for example, in configuration to receive one or more measurement devices (e.g., spectrometer, imaging device, etc.) to determine properties of the sample 502 of rock cuttings. The rock cutting sample 502 may reside or move along the platform 504 to be examined by different measurement devices of the 104.

A modular structure or support may physically receive and couple the measurement devices with the analyzer 104. Such a support framework may include communicative couplings or circuitry to facilitate computer-implemented control of the measurement devices. A conveyor may move and position the sample 502 in paths of respective measurement windows of the measurement devices.

Indeed, the mud-logger 102 may transport or convey (e.g., via a mechanical conveying belt or mesh, trough, rotating platform, etc.) the sample 502 along a path within the housing 106 through one or more measurement windows of respective measurement devices comprising the modular analyzer 104. The measurement devices may include a first measurement device such as a spectrometer (e.g., a laser-induced breakdown spectrometer) to determine the properties comprising an elemental composition of the sample of the rock cuttings substantially in real time with collection of the slurry sample. A measurement device residing in the modular analyzer 104 may include an NMR spectrometer to determine the properties including pore space size of the rock cuttings in the sample or identification of fluid in the sample, or a combination thereof. Further, one or more of the measurement devices received into the modular analyzer 104 may include or be an imaging device to perform, for example, image recognition as discussed above. The robotic mud-logger may include a computer system (e.g., 518) to control the analyzer 104 and its measurement devices.

Figure 6:
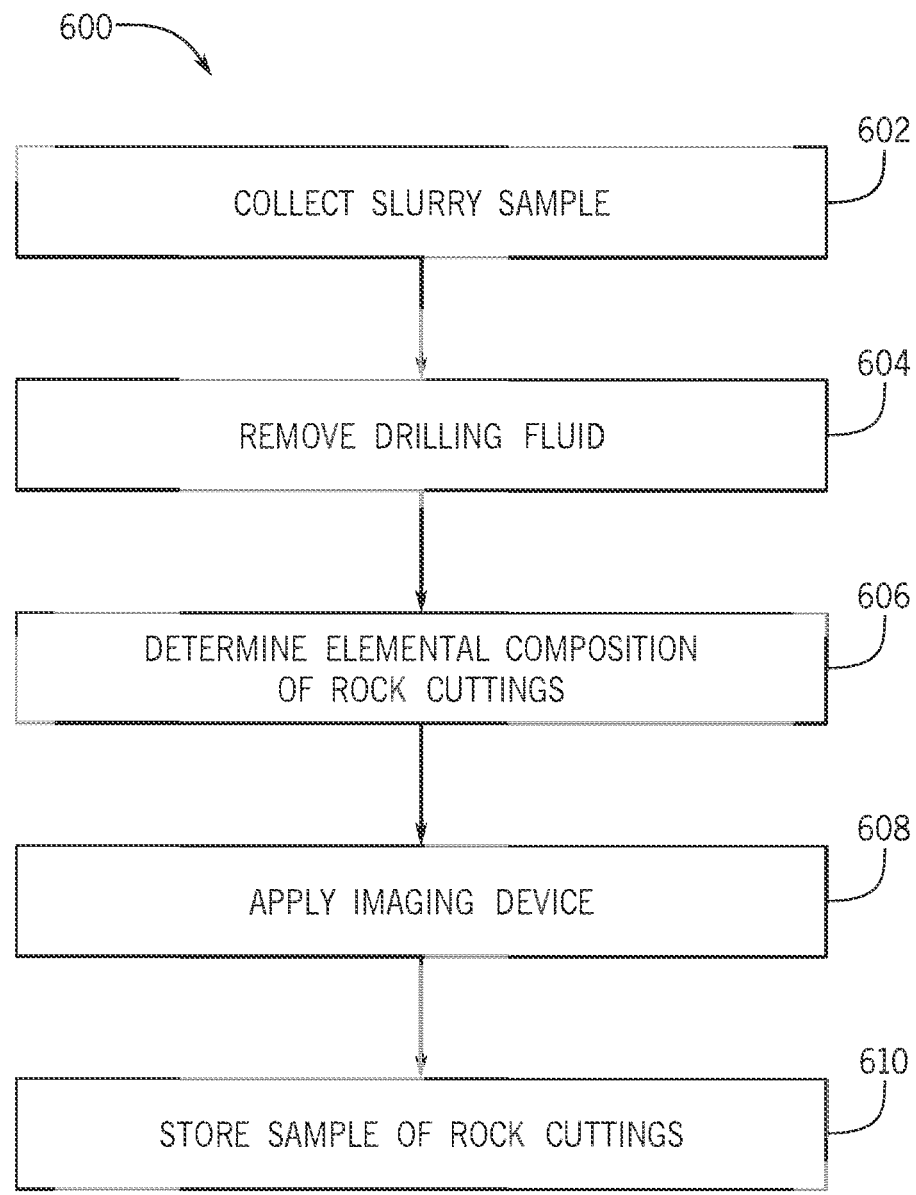
FIG. 6 depicts a block flow diagram of method of operating a robotic mud-logger in accordance with embodiments of the present techniques.

FIG. 6 depicts a schematic view of a method 600 of operating a robotic mud-logger to determine an elemental composition of a rock-cuttings sample. At block 602, the robotic mud-logger collects a slurry sample online from a drilling fluid system or circuit contemporaneous with drilling of a borehole. The slurry sample may include drilling fluid and rock cuttings. In examples, the sample point may be a flow conduit or shale shaker of the drilling fluid circuit. The method may include flowing the slurry sample from the slurry sampler through a collection conduit to a liquid separator of the robotic mud-logger.

At block 604, the method includes removing, via the liquid separator, drilling fluid from the slurry sample to give or discharge a sample of the rock cuttings, comprising substantially solid components. The method may include receiving the rock-cuttings sample from the liquid separator onto a platform of the robotic mud-logger, wherein the elemental composition is determined (e.g., via an analyzer or spectrometer) on the sample on the platform. In certain examples, a main housing of the robotic mud-logger encloses an analyzer and the platform. In particular examples, the robotic mud-logger and/or the housing of the robotic mud-logger may have an electrical classification per NFPA 70 of Class I, Division 1 or Class I, Division 2.

At block 606, the method includes determining, via the analyzer, an elemental composition of the sample substantially in real time with the collecting of the slurry sample, wherein the analyzer comprises a spectrometer in some examples. The robotic mud-logger may include a controller directing the analyzer and also directing the timing interval of the upstream slurry sample collection. The spectrometer may be a Raman spectrometer, a FTIR spectrometer, LIBS spectrometer, or other type of spectrometer. In certain examples, the elemental composition may be determined on the rock cuttings in native or collected form, e.g., without grinding or molding the rock cuttings.

At block 608, the method may include applying an imaging device of the robotic mud-logger to the sample. In other examples, an imaging device is not utilized. In one example, the method includes performing image recognition on the sample via the imaging device if employed. The image recognition may facilitate determination of size, shape, color, or texture, or any combinations thereof, of the rock cuttings in the sample.

Lastly, at block 610, the method may include storing the sample of the rock cuttings in the robotic mud-logger. Indeed, the method may include, for example, the robotic mud-logger removing or rotating the sample from the platform and storing the sample in a sample collection system such as on a collection reel or similar device. However, in other examples, a sample collection system is not employed and the sample is not stored but instead discharged, for example, as waste or return to the drilling fluid circuit.

Figure 7:
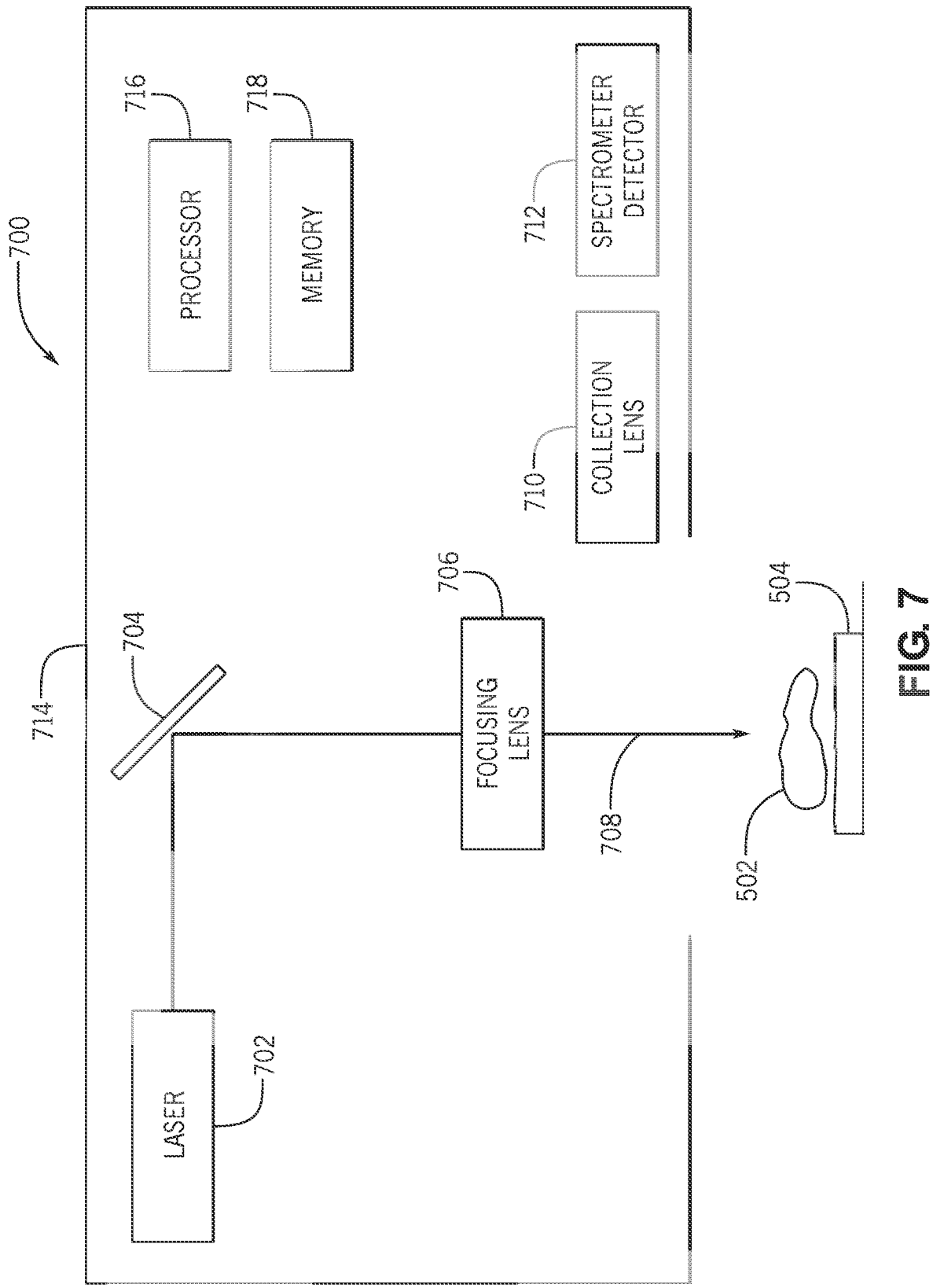
FIG. 7 depicts a block diagram of a laser-induced breakdown spectrometer of a robotic mud-logger in accordance with embodiments of the present techniques.

FIG. 7 depicts an example a laser-induced breakdown spectrometer 700 that may be part of the robotic mud-logger 102 discussed above with respect to the preceding figures. The laser-induced breakdown spectrometer 700 may be situated at the analyzer 104 (see FIGS. 1 and 5) or a component of the analyzer 104. In the illustrated embodiment of FIG. 7, the spectrometer 700 includes a laser-emitting device 702, mirror 704, and focusing lens 706 to apply a laser 708 to a rock-cuttings sample 502 disposed on a surface or platform 504. In the example depicted in FIG. 7, sample preparation of the sample 502 is not required. In operation, a short laser pulse may create a micro-plasma on the rock-cuttings sample 502 surface. Indeed, LIBS technology may involve formation of high-temperature plasma, induced by a short laser pulse. When the short-pulse laser beam is focused onto the sample 502 surface, a small volume of the sample mass is ablated, e.g., removed via both thermal and non-thermal mechanisms in a process known as laser ablation. The laser device 702 may be a solid-state laser, such as a high-power Nd:YAG laser. The Nd:YAG is neodymium$^{3+}$-doped yttrium aluminum garnet; Nd:Y$_3$Al$_5$O$_{12}$. As indicated, in operation, laser 708 is focused onto the sample 502 surface to produce plasma. Light from the plasma is captured by collection lens 710 and the spectrometer detector 712 to determine characteristic spectra identifying elements of the sample 502, allowing concentrations of elements in the sample to be measured. The analysis may be noninvasive and generally nondestructive. The Nd:YAG laser generates energy in the near infrared region of the electromagnetic spectrum, e.g., with a wavelength of 1064 nanometers (nm). The pulse duration may be in the region of 10 nanoseconds (ns) generating a power density which can exceed 1 GW•cm$^{-2}$ at the focal point. Other types of lasers may be employed for laser-induced breakdown spectroscopy, including those that generate energy in the visible and ultraviolet regions.

As indicated, the spectrometer 700 may operate by focusing laser 708 onto a small area at the surface of the sample 502. When laser 708 is discharged, laser 708 may ablate a very small amount of material of the sample 502, in the range of nanograms to picograms, which generates a plasma plume. In particular examples, the spectrometer 700 may include either a monochromator (scanning), e.g., Czerny-Turner type, or a polychromator (non-scanning), e.g., Echelle type, and a photomultiplier or CCD detector, respectively. Again, because such a small amount of material is typically consumed during the LIBS process, the technique may be considered essentially nondestructive or minimally-destructive. Further, with an average power density of less than one watt radiated onto the specimen or sample 502, there may be almost no sample 502 heating surrounding the ablation site. Moreover, due to the nature of this technique, sample preparation may be typically eliminated (or limited to homogenization). Indeed, sample preparation is often unnecessary where a specimen is known to be sufficiently homogenous. LIBS may also be a rapid technique giving results within seconds, making it particularly useful for high volume analyses or on-line industrial monitoring. LIBS is generally an optical technique and, therefore, generally only applies optical access to the specimen. As indicated, being an optical technique, the spectroscopy is generally non-invasive and non-contact. Additionally, LIBS systems can be coupled to an optical microscope for micro-sampling adding analytical flexibility. Moreover, examples of the laser-induced breakdown spectrometer 700 may typically not use ionizing radiation or radiation generally.

The elemental analysis may provide for an oxide weight percent for SiO2, TiO2, Al2O3, Fe2O3, MnO, MgO, CaO, Na2O, K2O, or P2O5, or any combinations thereof. The elemental analysis performed by the spectrometer 700 on the sample 502 may measure and provide for indication of trace elements (e.g., in parts per million or ppm), such as vanadium (V), chromium (Cr), cobalt (Co), nickel (Ni), zinc (Zn), gallium (Ga), arsenic (As), rubidium (Rb), strontium (Sr), yttrium (Y), zirconium (Zr), niobium (Nb), molybdenum (Mo), cesium (Cs), barium (Ba), lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), ytterbium (Yb), lutetium (Lu), hafnium (Hf), tantalum (Ta), thorium (Th), or uranium (U), or any combinations thereof. Such analysis may be a function of selectivity and detection limits, calibration results, and the like.

The spectrometer 700 may include or be associated with a processor 714 (e.g., microprocessor, CPU, etc.) and memory 716. The memory 716 may store code executed by the processor 714 to direct operation of the spectrometer and the determination of an elemental composition of the sample 502. In addition, the spectrometer 700 may be communicatively coupled to remote computer systems away from the drill site.

Furthermore, the robotic mud-logger 102, analyzer 104, or spectrometer 700 may include a sensor to detect presence of natural gas, methane, or other hydrocarbons within the spectrometer 700 or near the spectrometer 700. The sensor feedback may be coupled to the processor 714 or other computing system which may shutdown the spectrometer 700 in response to the sensed concentration exceeding a threshold such as a combustible or flammable threshold.

In addition, the spectrometer 700 may have an electrical classification per the National Electrical Code (NEC) or NFPA 70 of Class I, Division 1 or Class I, Division 2. In addition, or in the alternative, the spectrometer 700 may satisfy similar standards in the United States or Canada and from other countries and jurisdictions (e.g., United Kingdom, Europe, etc.) around the world. In one example in general, the robotic mud-logger or housing of the robotic mud-logger may have an electrical classification per National Fire Protection Association (NFPA 70) National Electrical Code §500.7 Protection Techniques. The spectrometer 700 may include conduit seals, explosion-proof enclosure, explosion-proof panelboard, explosion-proof fittings, mineral-insulated cable, metal-clad cable, intrinsically safe components such as intrinsically safe wiring or circuits, components encased or encapsulated in a resin type material, and so on. The phrases such as "explosion-proof" and "intrinsically safe" should not be taken in an absolute literal sense or too broadly based on plain language alone, but instead per the applicable industry or government standards.

Figure 8:
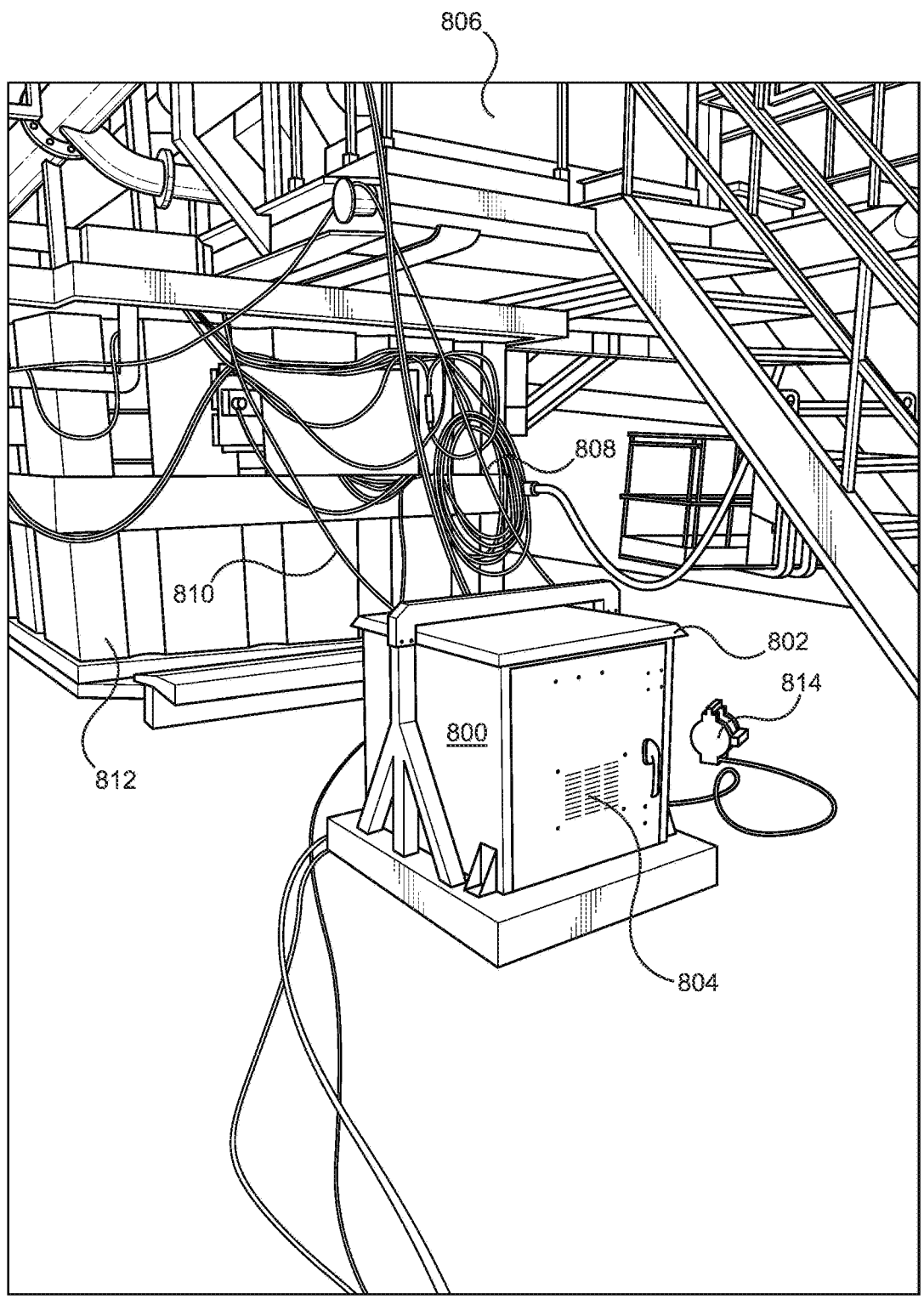
FIGS. 8, 9, 9A, 10 and 10A depict perspective views of robotic mud-loggers in accordance with embodiments of the present techniques.

FIG. 8 is a robotic or automated mud-logger 800 having a cabinet or housing 802 with a front door 804. In this depicted example, the mud-logger 800 is operationally coupled to a shale shaker 806 via a collection conduit 808, such as to the possum belly of the shale shaker 806. The shale shaker 806 may be a component of a drilling fluid system or circuit associated with drilling of a borehole. The automated mud-logger 800 may include an extractor or slurry collector disposed in the shale shaker 806 to sample a slurry of drilling fluid and rock cuttings from the shale shaker 806. The mud-logger 800 may transfer the slurry sample via the collection conduit 808 to a liquid separator in the housing 802. The liquid separator may remove drilling fluid from the slurry sample and discharge a rock-cuttings sample inside the housing 802 for analysis by a spectrometer or other analytical device of the robotic mud-logger 102. The automated mud-logger 800 may include a discharge conduit 810 to return removed drilling fluid to the shale shaker 806 or to the mud vessel 812 (such as a mud tank) below the shale shaker 806. In operation, the shale shaker 806 may discharge drilling fluid to the mud vessel 812. One or more motive devices 814 (e.g., pump) may facilitate flow of the slurry sample and the returned drilling fluid.

Figure 9:
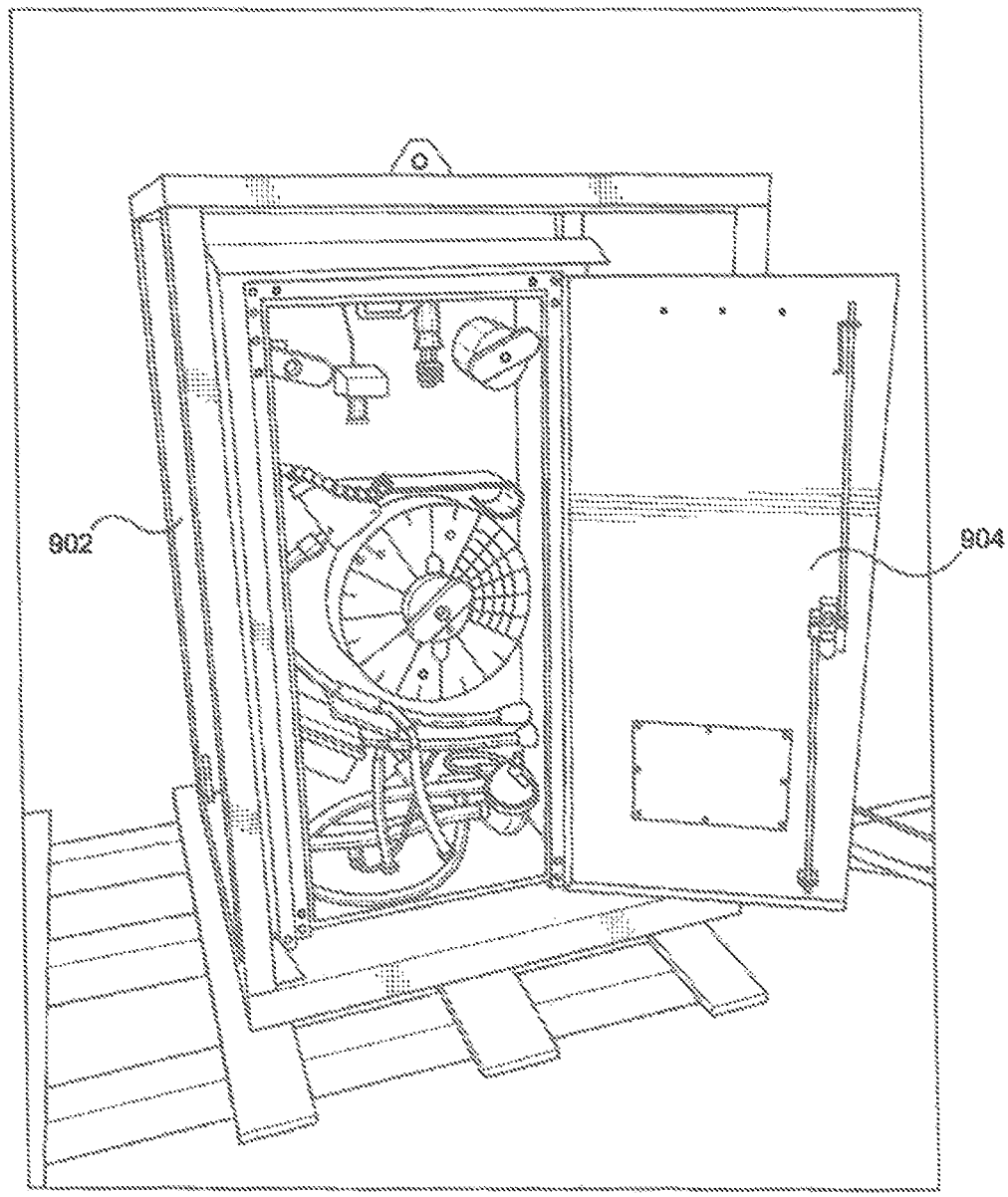
Figure 9A:
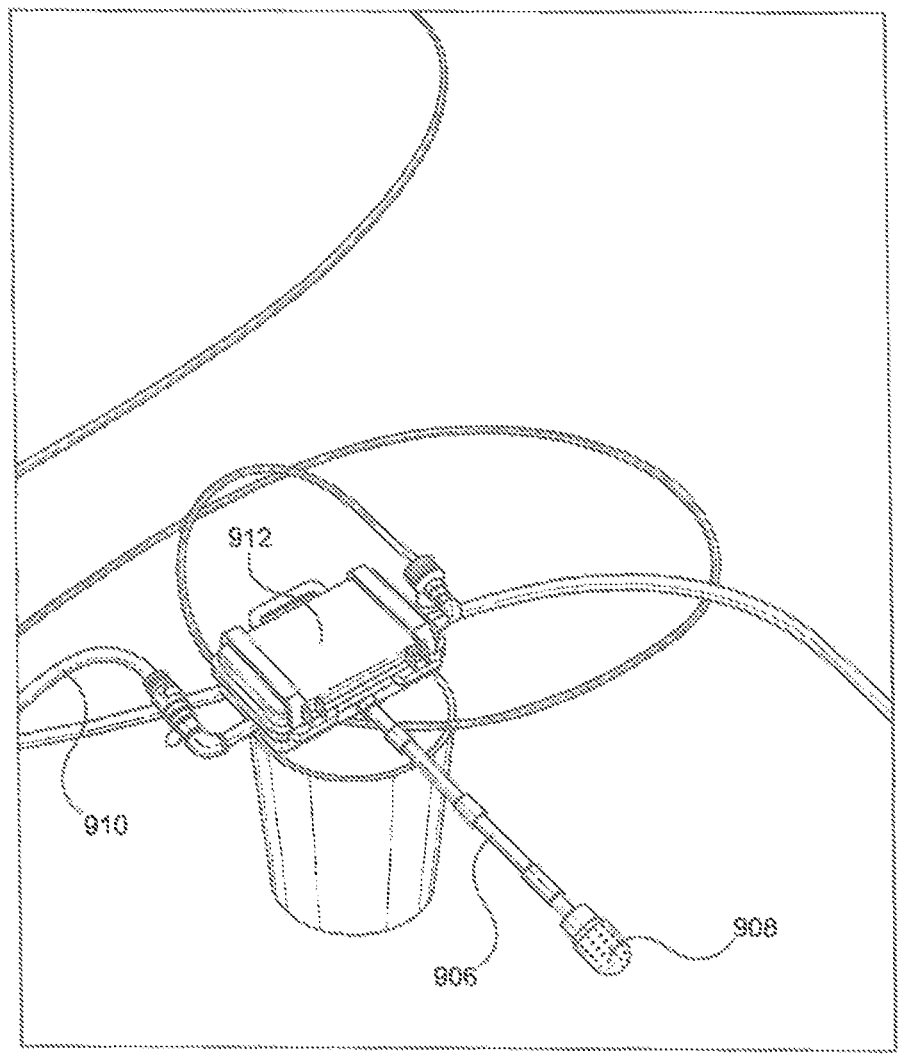

FIGS. 9 and 9A depict a robotic mud-logger 900 having a main housing 902 with a front door panel 904. Referring to FIG. 9A, mud-logger 900 also has an extractor or slurry collector 906 having a tip or shield 908 to prevent large particles from entering the slurry collector 906. The slurry collector 906 may be inserted into a drilling fluid system to extract a slurry sample of drilling fluid and rock cuttings, and discharge the slurry sample through a collection conduit 910 to the main housing 902 (depicted in FIG. 9). The robotic mud-logger 900 or extractor/slurry collector 906 may include a box 912 that is a sampling handling system. The box 912 may couple to multiple conduits including for sampling, purging, suction, and the like. In one example, the box 912 has a series of chambers and baffles that direct flow.

Figure 10:
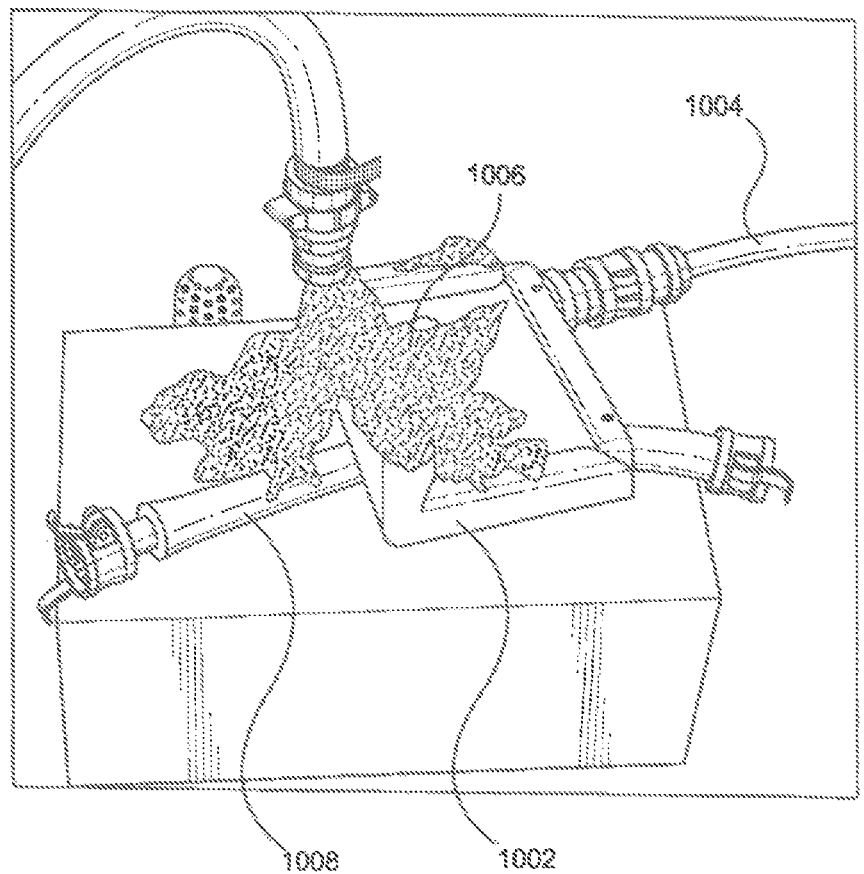
Figure 10A:
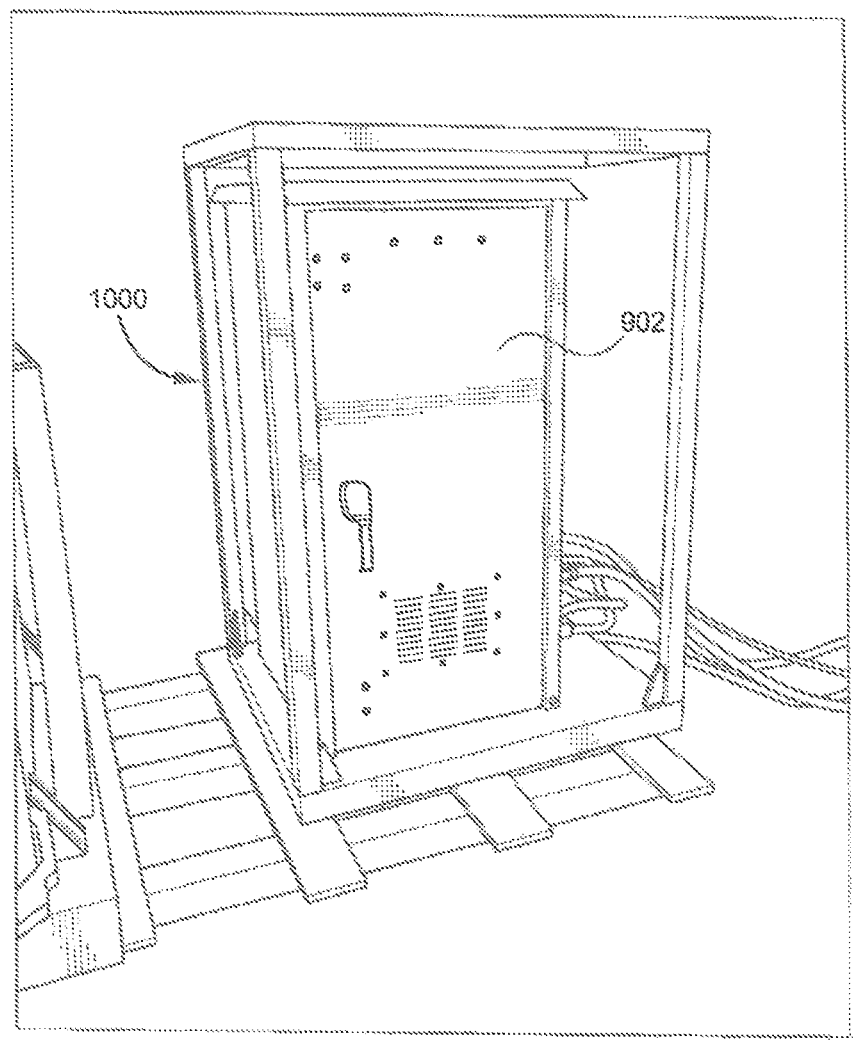

FIGS. 10 and 10A depict a robotic mud-logger 1000 having a main housing 902 and an extractor or sample collector 1002. In the depicted example, the sample collector 1002 includes or is a sample board. The sample collector 1002 may be inserted into a shale shaker (e.g., in the possum belly) or in another vessel of a drilling fluid system associated with drilling of a well bore or borehole. The mud-logger 1000 may utilize the slurry collector 1002 to sample a slurry of drilling fluid and rock cuttings, and transport the slurry sample via a collection conduit 1004 to the main housing 902. In the illustration, rock cuttings 1006 are situated on the slurry collector 1002 sample board. Lastly, the slurry collector 1002 or sample board may be coupled to additional conduits 1008.

Figure 11:
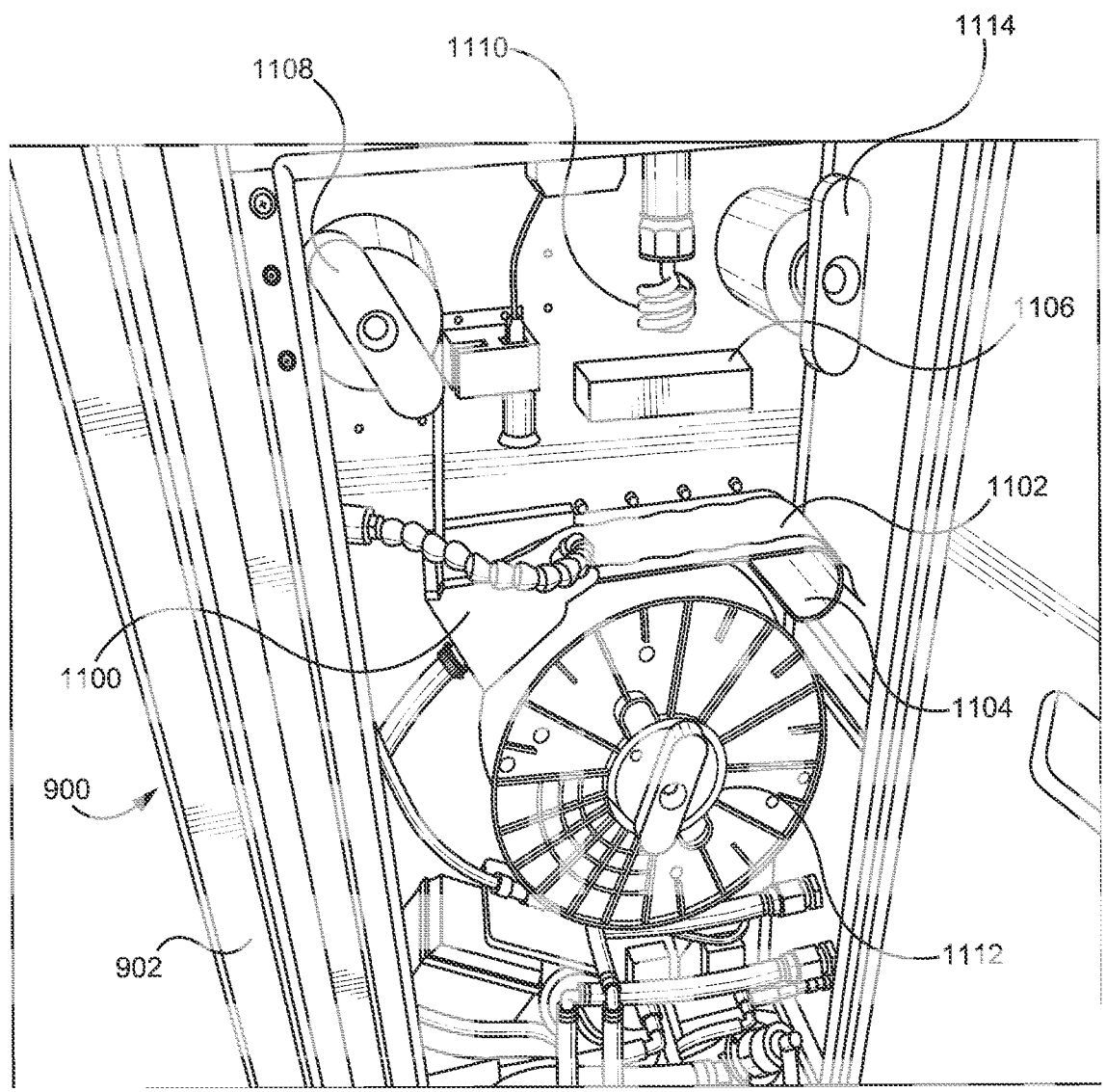
FIG. 11 depicts a perspective view of a main housing of the robotic mud-loggers of FIGS. 9, 9A, 10 and 10A with components disposed therein in accordance with embodiments of the present techniques.

FIG. 11 depicts the main housing 902 of the robotic mud-logger 900 and 1000, and with components disposed therein. The mud-logger includes a liquid separator 1100 which is this particular example includes cooperatively a sample collection device, a sample intake house, and an underlying mesh 1102. A slurry sample of drilling fluid and rock cuttings may enter the liquid separator 1100 which separates the drilling fluid through the mesh 1102, leaving the rock cuttings residing on top of the mesh 1102. In some examples, a vacuum may be implemented to pull the drilling fluid through the underlying mesh. Also, the tightness (e.g., pore size, void volume, etc.) of the mesh may be selected as desired.

After removal of the drilling fluid from the slurry sample, a rotation or conveying system of the mud-logger may rotate or move the mesh 1102 over the platform 1104, placing the rock cuttings residing on the mesh 1102 to be supported by the mesh 1102 and the platform 1104. The robotic mud-logger includes an analyzer 1106 (e.g., analogous to 104), such as a spectrometer, FTIR spectrometer, laser-induced breakdown spectrometer, etc. The analyzer 1106 may perform elemental analysis on the rock-cuttings sample on the mesh 1102 and platform 1104 to determine an elemental composition of the rock-cuttings sample. In addition, the mud-logger incudes an imaging device 1108 to capture digital photos of the rock-cuttings sample. The imaging device 1108 may include a microscope. The robotic mud-logger also employs the imaging device 1108 to perform image recognition on the rock-cuttings sample to determine size, shape, color, or texture of the rock cuttings in the sample. The robotic mud-logger includes a UV light source 1110 so that the imaging device 1108 can capture digital images of the rock cutting sample exposed to UV light.

Furthermore, the robotic mud-logger of FIG. 11 may include a sample collection system which in this instance may comprise a sample collection reel 1112 and a seal support 1114. In the illustrated example, the seal support 1114 may retain or hold a spool of sealant wrap. The sealant wrap can be applied to the cuttings samples as the cuttings samples are rotated onto the sample collection reel 1112. In certain embodiments, the sample collection reel 1112 along with the cutting samples stored therein may be removed from the robotic mud-logger and brought to a facility for inspection of the cuttings samples.

Lastly, the analyzer 1106 for certain embodiments of the automated or robotic mud-logger 900 and 1000 of FIG. 11 may be a modular device. In other words, the analyzer 1106 may be configured as a modular receptor to incorporate one or more measurement devices (e.g., spectrometers, imaging devices, etc.) to determine properties of the sample of rock cuttings on the mesh 1102 and platform 1104. The rock-cuttings sample may reside or move along the platform 1104 to be examined by different measurement devices of the analyzer 1106. A modular structure or support may physically receive and couple the measurement devices with the analyzer 1106. Such a support framework may include communicative couplings or circuitry to facilitate computer-implemented control of the measurement devices. A conveyor may move and position the sample in view of respective analysis windows of the measurement devices. In particular, the mud-logger may transport or convey (e.g., via a mechanical conveying belt or mesh 1102) the sample along a path (e.g., across the platform 1104) within the housing 900 through one or more measurement windows of respective measurement devices composing the modular analyzer 1106.

The received or incorporate modular measurement devices may include a first measurement device such as a spectrometer (e.g., a laser-induced breakdown spectrometer) to determine the properties comprising an elemental composition of the sample of the rock cuttings substantially in real time with collection of the slurry sample. A measurement device residing in the modular analyzer 1106 may also include an NMR spectrometer to determine the properties including pore space size of the rock cuttings in the sample or identification of fluid in the sample, or a combination thereof. Further, one or more of the measurement devices received into the modular analyzer 1106 may include or be an imaging device to perform, for example, image recognition as discussed above. The robotic mud-logger may include a computer system control the analyzer 1106 and its measurement devices.

Figure 12:
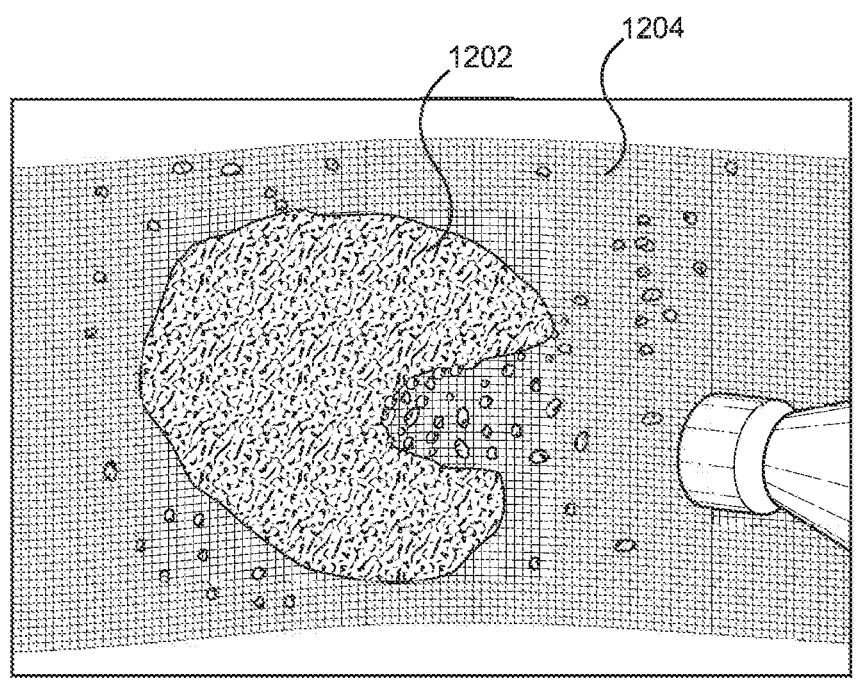
FIG. 12 depicts a perspective view of sample images depicting rock cuttings on a mesh of a robotic mud-logger in accordance with embodiments of the present techniques.

FIG. 12 depicts sample images 1200 depicting rock cuttings 1202 on a mesh 1204 of a robotic mud-logger. In examples, the images 1200 may be captured by an imaging device of the robotic mud-logger. A mesh may be a semi-barrier made of connected strands of metal, fiber, or other flexible or ductile materials. A mesh may have many attached or woven strands and be similar to a web or a net. Materials of construction of the mesh 1204 may include metal, steel, plastic, polypropylene, polyethylene, nylon, polyvinyl chloride (PVC), polytetrafluoroethylene (PTFE), fiberglass, etc.

Figure 13:
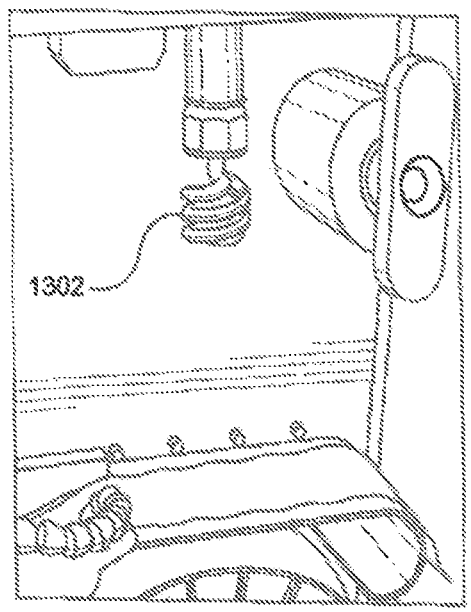
FIGS. 13 and 13A depict perspective views of aspects associated with a robotic mud-logger in accordance with embodiments of the present techniques.
Figure 13A:
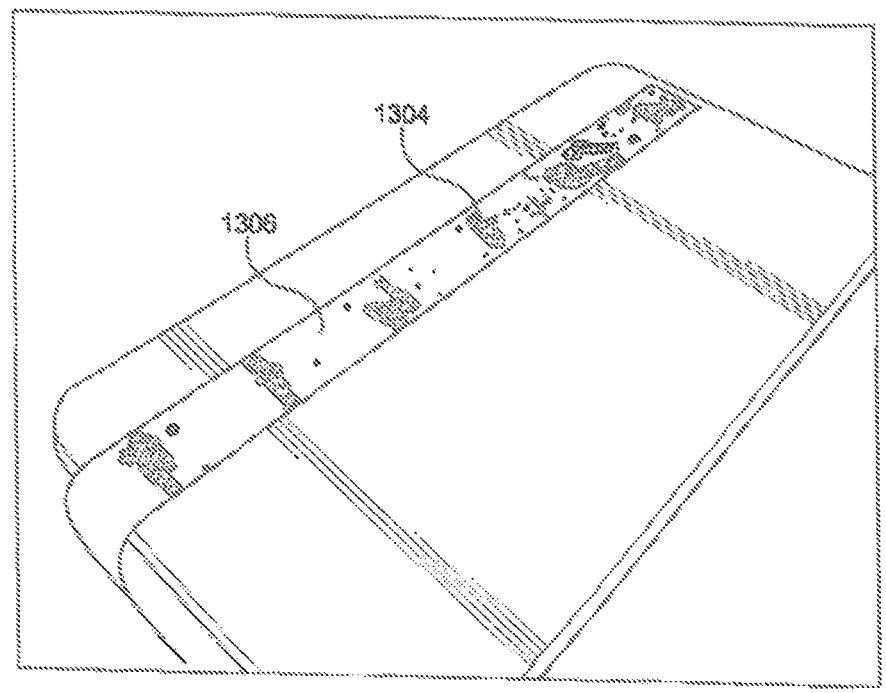

FIGS. 13 and 13A depict various aspects associated with a robotic mud-logger including a UV light source 1302 internal within a housing of the robotic mud-logger. The rock-cuttings samples 1304 collected and stored by the robotic mud-logger may be removed from the robotic mud-logger and laid out for inspection, as depicted in FIG. 13A. The spacing 1306 between the samples 1304 may be indicative of the sample frequency. For embodiments where the sample interval is substantially continuous (e.g., less than 5 or 10 seconds), the rock-cuttings samples 1304 may be a substantially continuous stream (with at most small gaps) across the surface or mesh as laid out. In any case, the inspection may be visual and may include, for example, analysis via a handheld XRF analyzer. In other examples, the online analyzer of the robotic mud-logger may provide for XRF analysis in real time.

Figure 14:
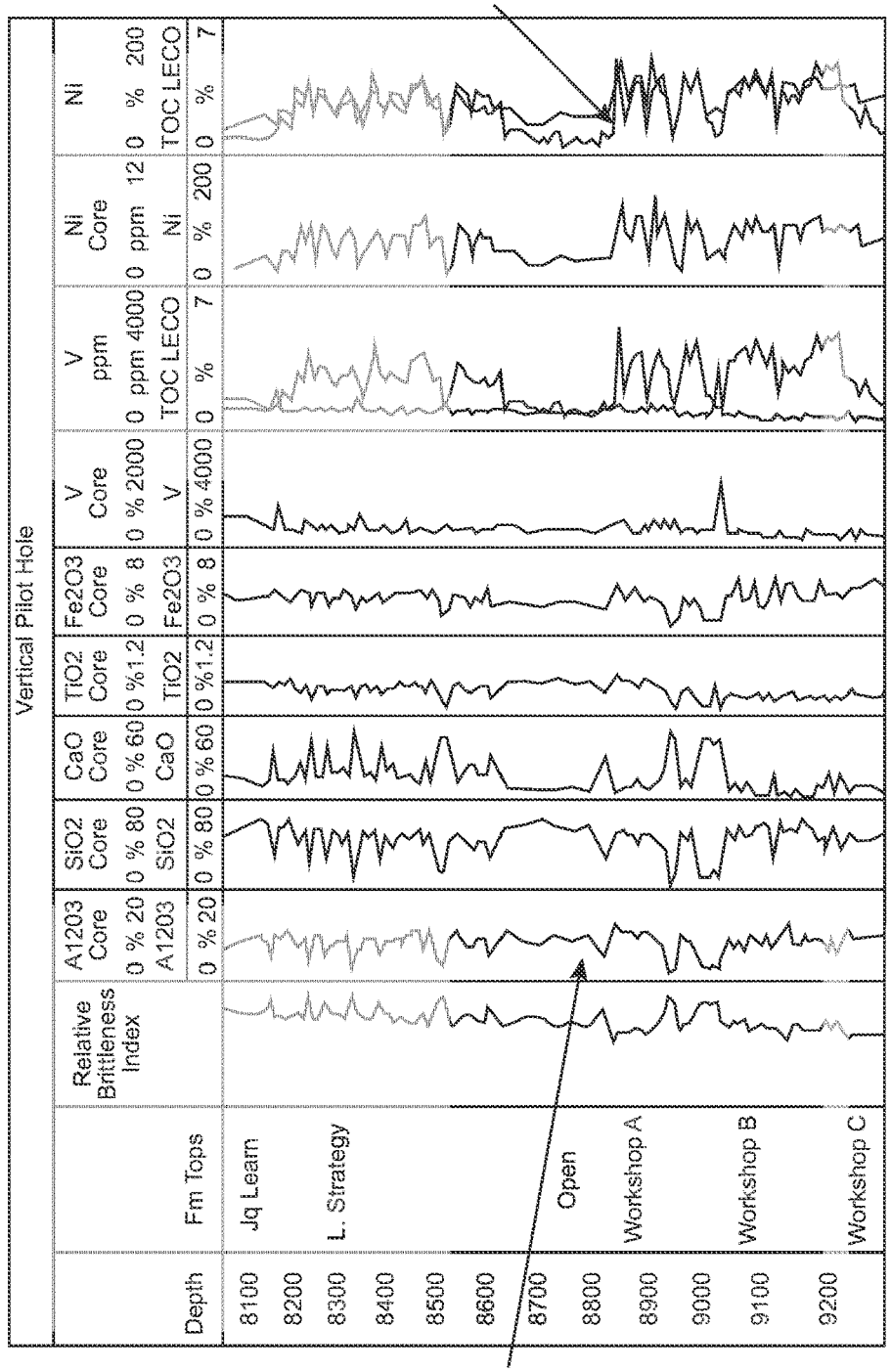
FIG. 14 depicts a diagrammatic depiction of a screenshot of displayed data highlighting the improved sample collection process of the automated system (robotic mud-logger) of the present invention compared to conventional techniques and compares XRF elemental compositions from a core to samples collected by the robotic mud-logger of the present invention.

FIG. 14 depicts a diagrammatic depiction of a screenshot of displayed data highlighting the improved sample collection process of the automated system (robotic mud-logger) of the present invention compared to conventional techniques and compares XRF elemental compositions from a core to samples collected by the robotic mud-logger of the present invention.

Figure 14A:
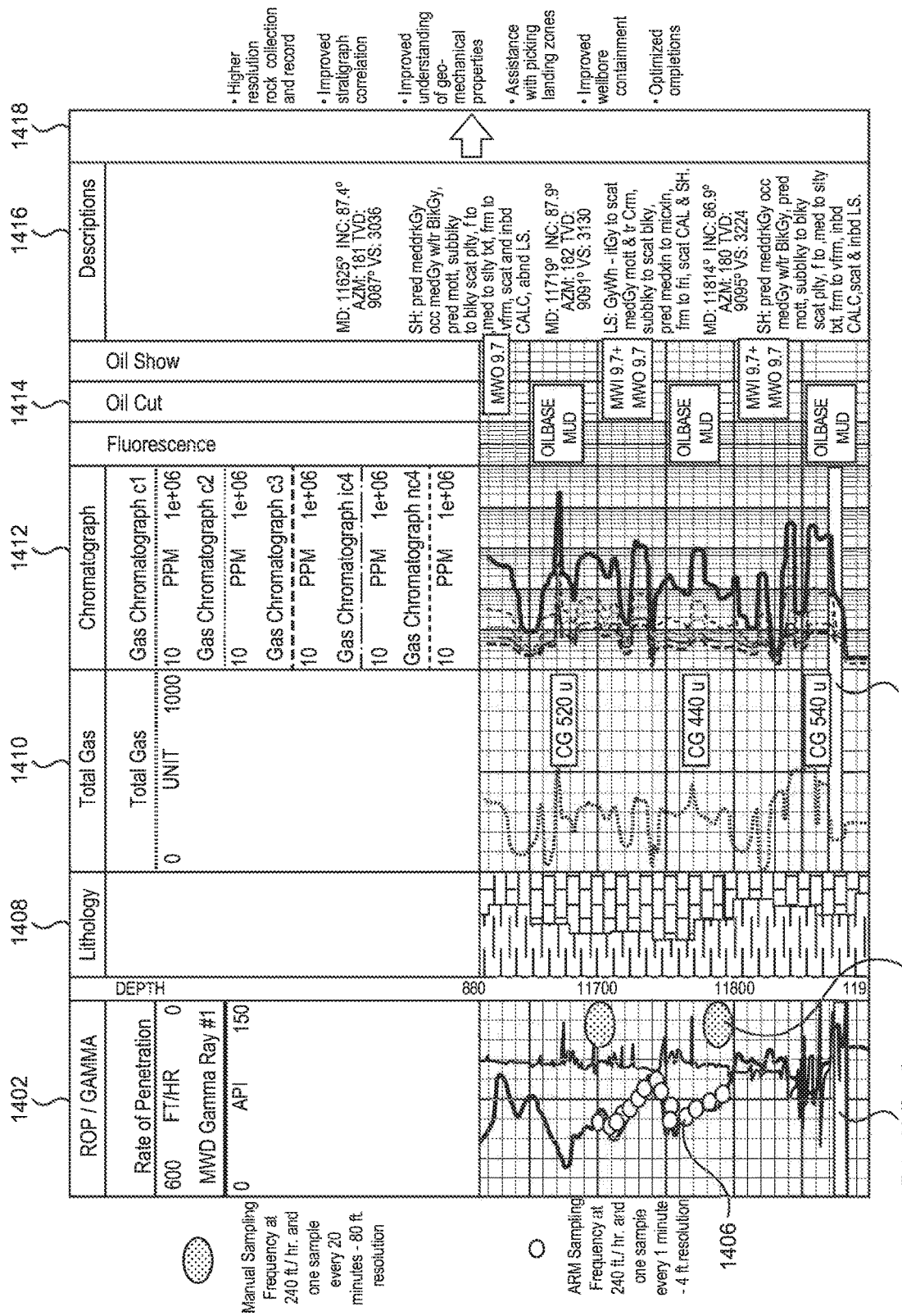
FIG. 14A depicts improved sample collection resolution with increased frequency of samples per depth interval.

FIG. 14A depicts a screenshot 1400 of a display of data collected or generated at least in part by a robotic mud-logger or computing systems associated with a robotic mud-logger. The first column 1402 indicates a sample frequency of the slurry sample having the drilling fluid and rock cuttings. Manual sampling frequency is indicated by the larger dots 1404. The automated sampling by the robotic mud-logger gives a significantly greater frequency, as indicated by the smaller dots 1406. In general, as shown by the screenshot 1400, the displayed data or data output/results may be in text and graphical form, and given in columns 1402, 1408, 1410, 1412, 1414, 1416, and 1418. The column 1418 may depict the element composition results of the elemental analysis of the rock-cuttings samples by the robotic mud-logger. Such data may also be presented to the user in other formats.

Figure 15:
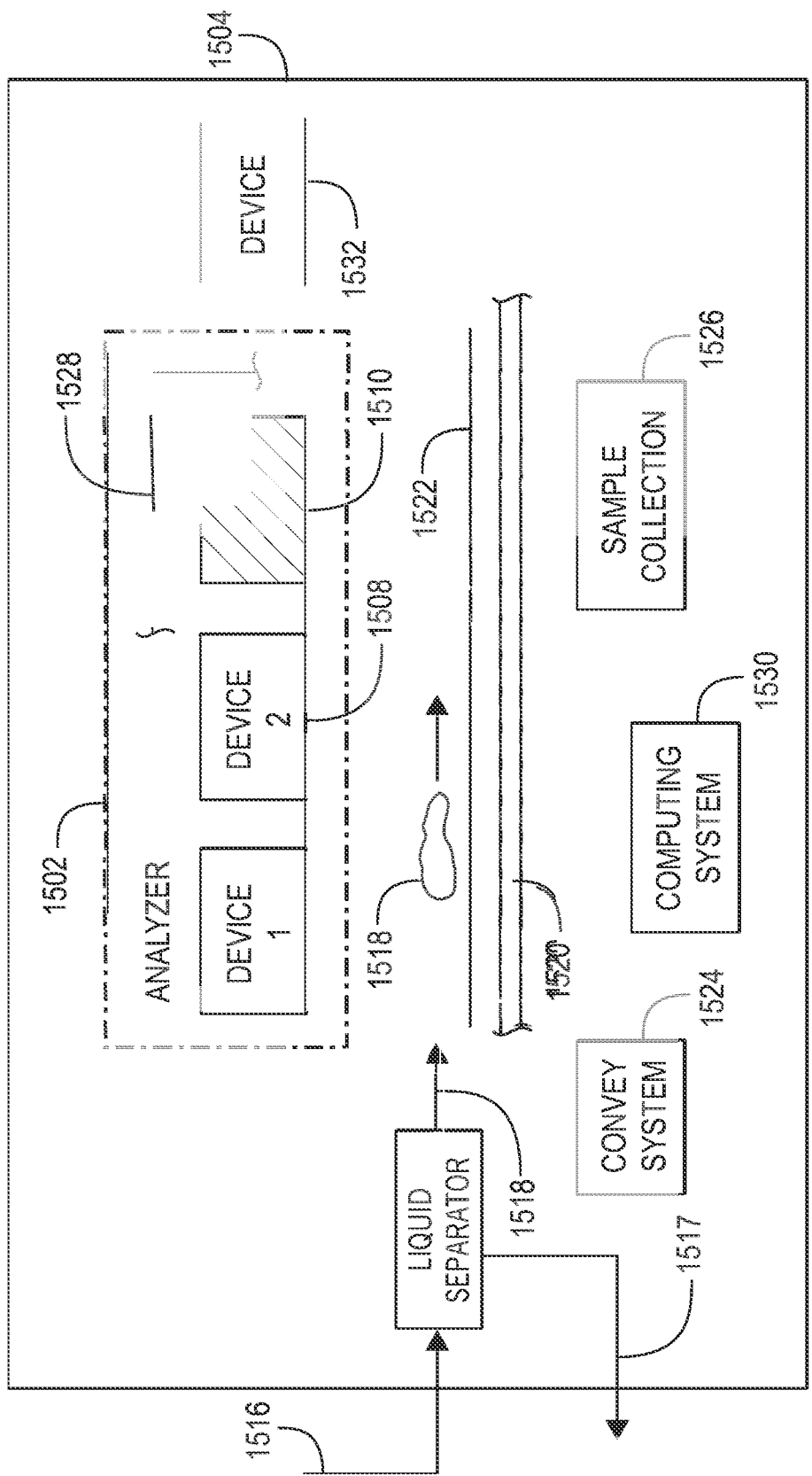
FIG. 15 depicts a diagram of a robotic mud-logger having a modular analyzer in accordance with embodiments of the present techniques.

FIG. 15 is an automated or robotic mud-logger 1500 that may collect and analyze rock cuttings discharged from a well borehole being drilled. The mud logger 1500 may sample a slurry of drilling fluid and rock cuttings from a drilling fluid system being employed in the drilling of the borehole. The robotic mud-logger 1500 may determine properties of the sampled rock cuttings (drill cuttings).

Indeed, the robotic mud-logger 1500 includes an analyzer 1502 in a cabinet or housing 1504 to determine at least an elemental composition of the rock cuttings. This example of an analyzer 1502 may receive multiple measurement devices that analyze the rock cuttings to determine properties of the rock cuttings. Thus, the analyzer 1502 may be characterized as a modular analyzer in some embodiments. In the illustrated embodiment, a first measurement device 1506 and a second measurement device 1508 are disposed or mounted in the analyzer 1502. Also, the analyzer 1502 has a cavity or mount 1510 to receive a third measurement device. Further, the analyzer 1502 may have an analyzer housing 1512.

In this example, the robotic mud-logger 1500 has a liquid separator 1514 to receive a slurry sample 1516 collected from a drilling fluid circuit associated with the drilling of the well borehole. For example, the slurry sample 1516 may be collected from a return conduit or shale shaker of the drilling fluid system. The mud logger 1500 may include a slurry sampler (not shown) to be installed inserted into a flow conduit or shale shaker of the drilling fluid circuit to collect the slurry sample 1516. The robotic mud-logger 1500 via its slurry sampler may collect a slurry sample 1516 online from the drilling fluid circuit contemporaneous with drilling of the borehole. The slurry sample 1516 may generally include drilling fluid and rock cuttings. In operation, the liquid separator 1514 removes drilling fluid 1517 from the slurry sample 1516 and discharges a rock-cuttings sample 1518.

In some examples, the separator 1514 may discharge the rock-cuttings sample 1518 onto a surface or platform 1520 in the robotic mud-logger 1500. In the illustrated example, the sample 1518 is discharged onto a conveying belt 1522 which transports the rock-cuttings sample 1518 along the platform 1520. The conveying belt 1522 may be a component of a transport or mechanical conveying system 1524. Other types of transport or conveying systems may be employed. Moreover, in one example, the conveying belt 1522 is a mesh that may cooperatively be a component of the liquid separator 1514 to facilitate removal of the drilling fluid 1517 from the slurry sample 1516. In certain examples, the conveying belt 1522 may route the rock-cuttings sample 1518 to a sample collection system 1526 of the robotic mud-logger 1500, if a sample collection system 1526 is employed.

The analyzer 1502 may include a frame or modular support 1528 to physically receive the measurement devices. The support 1528 may also facilitate communication of the measurement devices with a computing system 1530 of the robotic mud-logger 1500 to enable computer-implemented control of the measurement devices. The computing system 1530 may include a hardware processor and memory to store code executable by the processor to direct the measurement devices in operation. The mud logger 1500 may also include one or more measurement devices 1532 separate from the analyzer 1502 to determine properties of the rock-cuttings sample 1518.

The disposed measurement devices 1506, 1508, 1552 and any measurement devices to be received to the modular analyzer 1502 such as into the cavity 1510 of the analyzer 1502 may be various types of devices. For example, the measurement devices may include a spectrometer (e.g., LIBS, FTIR, etc.) to measure an elemental composition of the sample 1518, an NMR device to determine pore space size of the rock cuttings or identify a fluid in the sample 1518, an imaging device to perform image recognition on the sample 1518, and so forth. The measurement devices may determine properties of the rock cuttings in the sample 1518 substantially in real time with collection of the slurry sample 1516 from the drilling fluid system.

In operation for some examples, the conveyor (e.g., conveying belt 1522) of a conveying system 1524) moves the rock-cuttings sample 1518 along the platform 1520 under or adjacent the analyzer 1502 so that each measurement device may analyze the rock-cuttings sample 1518. The conveyor may move and position the sample 1518 in paths of respective measurement windows of the measurement devices. In certain examples, the robotic mud-logger 1500 does not grind or mold the sample 1518 of rock cuttings. In other words, examples of the robotic mud-logger 1500 do not include a sample preparation system that grinds or molds, or otherwise prepares, the sample 1518 of rock cuttings for analysis. The liquid separator 1514 may remove drilling fluid 1517 but the rock cuttings in the sample 1518 are analyzed as collected from the well borehole.

In conclusion, an oil well may be a boring in the earth designed to bring petroleum oil hydrocarbons to the surface. Typically, some natural gas is released along with the oil. A well that produces primarily or only natural gas may be termed a gas well. Before a well is drilled, a geologic target may be identified by a geologist or geophysicist to meet the objectives of the well. For a production well, the target may be picked to promote production from the well and manage reservoir drainage. For an exploration or appraisal well, the target may be chosen to confirm the existence of a viable hydrocarbon reservoir or to ascertain extent. For an injection well, the target may be selected to locate the point of injection in a permeable zone, which may support disposing of water or gas or pushing hydrocarbons into nearby production wells, and the like. The target or the end point of the well may be matched with a surface location or starting point of the well, and a trajectory between the two designed. When the well path is identified, a team of geoscientists and engineers may develop a set of presumed properties of the subsurface that will be drilled through to reach the target. These properties include pore pressure, fracture gradient, wellbore stability, porosity, permeability, lithology, faults, and mineral content. This set of assumptions may be used by a well engineering team to perform the casing design and completion design for the well, and for selection of the drill bit and drilling fluid.

The well may be created by drilling a hole (e.g. 5 inches to 40 inches in diameter) into the earth with a drilling rig that rotates a drill string with a bit attached. After the hole is drilled, sections of steel pipe or casing, slightly smaller in diameter than the borehole, may be placed in the hole. Cement may be placed between the outside of the casing and the borehole known as the annulus. The casing may provide structural integrity. In some examples, the drill bit aided by the weight of thick walled pipes called drill collars cuts into the rock. There are different types of drill bit. For instance, some cause the rock to disintegrate by compressive failure, while others shear slices off the rock as the bit turns, and so forth.

Drilling fluid (or "mud") is typically pumped down the inside of the drill pipe and exits at the drill bit. Components of drilling fluid may include water, clay, and/or a complex mixture of fluids, solids and chemicals tailored to provide the desired physical and chemical characteristics for drilling the well. Particular functions of the drilling mud include cooling the bit, lifting rock cuttings to the surface, preventing or reducing destabilization of the rock in the wellbore walls, generally overcoming the pressure of fluids inside the rock so that these fluids do not enter the wellbore, and so forth. Some oil wells are drilled with air or foam as the drilling fluid. The drilling rig typically contains equipment to circulate the drilling fluid, hoist and turn the pipe, control downhole, remove cuttings from the drilling fluid, and generate on-site power for these operations.

The generated rock cuttings may be swept up by the drilling fluid circulating back to surface outside the drill pipe. In some examples, the fluid may then go through shakers which strain the cuttings from the drilling fluid which is returned to the pit. Watching for abnormalities in the returning cuttings and monitoring pit volume or rate of returning fluid may be beneficial. A mud log or mud logging may study and report the lithology and other variable during drilling of oil wells. After drilling and casing the well, the well may be completed. Completion may be the process in which the well is enabled to produce oil or gas. The subsequent production stage may be when the oil and gas are produced.

Some embodiments may be implemented in one or a combination of hardware, firmware, and software. Some embodiments may also be implemented as instructions stored on a machine-readable medium, which may be read and executed by a computing platform to perform the operations described herein. A machine-readable medium may include any mechanism for storing or transmitting information in a form readable by a machine, e.g., a computer. For example, a machine-readable medium may include read only memory (ROM); random access memory (RAM); magnetic disk storage media; optical storage media; flash memory devices; or electrical, optical, acoustical or other form of propagated signals, e.g., carrier waves, infrared signals, digital signals, or the interfaces that transmit and/or receive signals, among others.

An embodiment is an implementation or example. Reference in the specification to "an embodiment", "one embodiment", "some embodiments", "various embodiments," or "other embodiments" means that a particular feature, structure, or characteristic described in connection with the embodiments is included in at least some embodiments, but not necessarily all embodiments, of the present techniques. The various appearances of "an embodiment," "one embodiment," or "some embodiments" are not necessarily all referring to the same embodiments. Elements or aspects from an embodiment can be combined with elements or aspects of another embodiment.

Not all components, features, structures, characteristics, etc. described and illustrated herein need be included in a particular embodiment or embodiments. If the specification states a component, feature, structure, or characteristic "may", "might", "can" or "could" be included, for example, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

It is to be noted that, although some embodiments have been described in reference to particular implementations, other implementations are possible according to some embodiments. Additionally, the arrangement and/or order of circuit elements or other features illustrated in the drawings and/or described herein need not be arranged in the particular way illustrated and described. Many other arrangements are possible according to some embodiments.

In each system shown in a figure, the elements in some cases may each have a same reference number or a different reference number to suggest that the elements represented could be different and/or similar. However, an element may be flexible enough to have different implementations and work with some or all of the systems shown or described herein. The various elements shown in the figures may be the same or different. Which one is referred to as a first element and which is called a second element is arbitrary.

It is to be understood that specifics in the aforementioned examples may be used anywhere in one or more embodiments. For instance, all optional features of a computing device described above may also be implemented with respect to either of the methods described herein or a computer-readable medium. Furthermore, although flow diagrams and/or state diagrams may have been used herein to describe embodiments, the present techniques are not limited to those diagrams or to corresponding descriptions herein. For example, flow need not move through each illustrated box or state or in exactly the same order as illustrated and described herein.

The present techniques are not restricted to the particular details listed herein. Indeed, those skilled in the art having the benefit of this disclosure will appreciate that many other variations from the foregoing description and drawings may be made within the scope of the present techniques. Accordingly, it is the following claims including any amendments thereto that define the scope of the present techniques.

The invention claimed is:

1. A robotic mud-logger comprising:
   a) a slurry sampler configured to collect a slurry sample online from a flow conduit or shale shaker of a drilling fluid circuit contemporaneous with drilling of a borehole, said slurry sample comprising drilling fluid and rock cuttings;
   b) a liquid separator configured to receive said collected slurry sample and remove drilling fluid from said collected slurry sample, and discharge a rock cuttings sample;
   c) a conduit configured to convey said slurry sample from said slurry sampler to said liquid separator;
   d) a spectrometer configured to receive said rock cuttings sample discharged from said liquid separator and perform elemental analysis of said rock cuttings sample; and
   e) conveyer configured to move said discharged rock cuttings sample from said liquid separator to said spectrometer.

2. The robotic mud-logger of claim 1, further comprising a storage device for receiving said rock cuttings sample from said spectrometer and storing said rock cuttings sample for future retrieval.

3. The robotic mud-logger of claim 1, wherein the spectrometer comprises a laser-induced breakdown spectrometer.

4. The robotic mud-logger of claim 3, wherein the laser-induced breakdown spectrometer comprises an electrical classification per National Fire Protection Association (NFPA) 70 of Class I, Division 1 or Class I, Division 2.

5. The robotic mud-logger of claim 4, wherein the computing system directs the spectrometer.

6. The robotic mud-logger of claim 1, wherein the elemental analysis comprises an oxide weight percent for silicon dioxide (SiO2), titanium dioxide (TiO2), aluminum oxide (Al2O3), iron(III) oxide (Fe2O3), manganese oxide (MnO), magnesium oxide (MgO), calcium oxide (CaO), sodium oxide (Na2O), potassium oxide (K2O), or phosphorous pentoxide (P2O5), or any combinations thereof. Wherein the trace elements comprise vanadium (V), chromium (Cr), cobalt (Co), nickel (Ni), zinc (Zn), gallium (Ga), arsenic (As), rubidium (Rb), strontium (Sr), yttrium (Y), zirconium (Zr), niobium (Nb), molybdenum (Mo), cesium (Cs), barium (Ba), lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), ytterbium (Yb), lutetium (Lu), hafnium (Hf), tantalum (Ta), thorium (Th), or uranium (U), or any combinations thereof.

7. The robotic mud-logger of claim 1, further comprising a computing system to control operation of the robotic mud-logger, the operation comprising sample handling and the spectrometer determining the elemental composition.

8. A drilling fluid system comprising:
a) a drilling fluid circuit to circulate drilling fluid through a drilling rig at a borehole during drilling of the borehole; and
b) an automated mud-logger comprising:
i) a slurry collector to acquire online a slurry sample of a drilling fluid slurry from the drilling fluid circuit, the drilling fluid slurry comprising drilling fluid and rock cuttings;
ii) a liquid separator to remove drilling fluid from the slurry sample and discharge a sample of the rock cuttings;
iii) a conduit coupling the slurry sampler to the liquid separator;
iv) an analyzer comprising a spectrometer to determine an elemental composition of the sample of rock cuttings; and
v) a conveyor for delivering said sample of rock cuttings from said liquid separator to said analyzer.

9. The drilling fluid system of claim 8, further comprising a storage device for receiving said sample of rock cuttings from said analyzer and storing said rock cuttings sample for future retrieval.

10. The drilling fluid system of claim 8, wherein the automated mud-logger comprises a hardware processor and memory storing code executable by the hardware processor to control sample handling by the automated mud-logger and to determine, via the analyzer, the elemental composition of the rock cuttings in native form as recovered from the borehole, wherein the elemental composition comprises an oxide weight percent.

11. The drilling fluid system of claim 10, further comprising a housing enclosing the analyzer and the computing system, wherein the housing comprises an electrical classification per National Fire Protection Association (NFPA) 70 of Class I, Division 1 or Class I, Division 2.

12. The drilling fluid system of claim 8, wherein the spectrometer comprises a Raman spectrometer, a Fourier-transform infrared (FTIR) spectrometer, or a laser-induced breakdown (LIBS) spectrometer or an imaging device to perform image recognition on the sample and wherein a housing encloses the analyzer and the platform.

13. The drilling fluid system of claim 8, further comprising a platform to support the sample of rock cuttings discharged from the liquid separator and a LIBS sample analyzer.

14. The drilling fluid system of claim 8, further comprising a sample preparation system configured to mold the sample of rock cuttings prior to delivery of said sample or rock cuttings to said analyzer.

15. A robotic mud-logger comprising:
a) a slurry sampler configured to collect a slurry sample online from a flow conduit or shale shaker of a drilling fluid circuit contemporaneous with drilling of a borehole, said slurry sample comprising drilling fluid and rock cuttings;
b) a liquid separator configured to receive said collected slurry sample and remove drilling fluid from said collected slurry sample, and discharge a rock cuttings sample;
c) a conduit coupling said slurry sampler to said liquid separator;
d) a housing;
e) a spectrometer disposed within said housing configured to receive said rock cuttings sample discharged from said liquid separator and perform elemental analysis of said rock cuttings sample; and
f) conveyer configured to move said discharged rock cuttings sample from said liquid separator to said spectrometer.

16. The robotic mud-logger of claim 15, further comprising a storage device for receiving said rock cuttings sample from said spectrometer and storing said rock cuttings sample for future retrieval.

17. The robotic mud-logger of claim 15, wherein the spectrometer comprises a laser-induced breakdown spectrometer.

18. The robotic mud-logger of claim 17, wherein the laser-induced breakdown spectrometer comprises an electrical classification per National Fire Protection Association (NFPA) 70 of Class I, Division 1 or Class I, Division 2.

19. The robotic mud-logger of claim 15, wherein the elemental analysis comprises an oxide weight percent for silicon dioxide (SiO2), titanium dioxide (TiO2), aluminum oxide (Al2O3), iron(III) oxide (Fe2O3), manganese oxide (MnO), magnesium oxide (MgO), calcium oxide (CaO), sodium oxide (Na2O), potassium oxide (K2O), or phosphorous pentoxide (P2O5), or any combinations thereof. Wherein the trace elements comprise vanadium (V), chromium (Cr), cobalt (Co), nickel (Ni), zinc (Zn), gallium (Ga), arsenic (As), rubidium (Rb), strontium (Sr), yttrium (Y), zirconium (Zr), niobium (Nb), molybdenum (Mo), cesium (Cs), barium (Ba), lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), ytterbium (Yb), lutetium (Lu), hafnium (Hf), tantalum (Ta), thorium (Th), or uranium (U), or any combinations thereof.

20. The robotic mud-logger of claim 15, further comprising a computing system to control operation of the robotic mud-logger, the operation comprising sample handling and the spectrometer determining the elemental composition.

\* \* \* \* \*